United States Patent
Bruchman et al.

(10) Patent No.: US 11,872,122 B2
(45) Date of Patent: *Jan. 16, 2024

(54) METHODS FOR IMPROVED PROSTHETIC HEART VALVE WITH LEAFLET SHELVING

(71) Applicant: EDWARDS LIFESCIENCES CORPORATION, Irvine, CA (US)

(72) Inventors: William C. Bruchman, Camp Verde, AZ (US); Cody L. Hartman, Flagstaff, AZ (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 723 days.

This patent is subject to a terminal disclaimer.

(21) Appl. No.: 16/852,825

(22) Filed: Apr. 20, 2020

(65) Prior Publication Data

US 2020/0246137 A1    Aug. 6, 2020

Related U.S. Application Data

(60) Continuation of application No. 15/720,441, filed on Sep. 29, 2017, now Pat. No. 10,660,745, which is a continuation of application No. 14/792,380, filed on Jul. 6, 2015, now Pat. No. 9,827,089, which is a division of application No. 13/869,878, filed on Apr. 24, 2013, now Pat. No. 9,101,469.

(60) Provisional application No. 61/739,721, filed on Dec. 19, 2012.

(51) Int. Cl.
*A61F 2/24* (2006.01)

(52) U.S. Cl.
CPC .......... *A61F 2/2409* (2013.01); *A61F 2/2412* (2013.01); *A61F 2/2415* (2013.01); *A61F 2/2418* (2013.01); *A61F 2230/0023* (2013.01); *A61F 2230/0026* (2013.01); *A61F 2240/001* (2013.01)

(58) Field of Classification Search
None
See application file for complete search history.

(56) References Cited

U.S. PATENT DOCUMENTS

| 654,799 A | 7/1900 | Levett |
| 3,739,402 A | 6/1973 | Kahn et al. |
| 3,938,197 A * | 2/1976 | Milo ..................... A61F 2/2403 623/2.21 |
| 3,953,566 A | 4/1976 | Gore |

(Continued)

FOREIGN PATENT DOCUMENTS

| AU | 2013363172 A1 | 7/2015 |
| AU | 2017202405 A1 | 4/2017 |

(Continued)

OTHER PUBLICATIONS

Norman E. Clough. Introducing a New Family of GORE (Trademark) ePTFE Fibers (2007).

(Continued)

*Primary Examiner* — Leslie Lopez
(74) *Attorney, Agent, or Firm* — Edwards Lifesciences

(57) ABSTRACT

Described embodiments are directed toward prosthetic valve leaflets of particular configurations that control bending character. In embodiments provided herein, valve leaflets are operable to bend along a base of the valve leaflets.

19 Claims, 21 Drawing Sheets

(56) References Cited

U.S. PATENT DOCUMENTS

| | | | |
|---|---|---|---|
| 4,053,084 A * | 10/1977 | Anderson | F16J 13/00 |
| | | | 220/268 |
| 4,178,639 A | 12/1979 | Bokros | |
| 4,187,390 A | 2/1980 | Gore | |
| 4,222,126 A | 9/1980 | Boretos et al. | |
| 4,265,694 A | 5/1981 | Boretos et al. | |
| 4,332,035 A | 6/1982 | Mano | |
| 4,340,091 A | 7/1982 | Skelton et al. | |
| 4,477,930 A | 10/1984 | Totten | |
| 4,556,996 A * | 12/1985 | Wallace | A61F 2/2412 |
| | | | 623/2.2 |
| 4,626,255 A | 12/1986 | Reichart et al. | |
| 4,759,759 A | 7/1988 | Walker et al. | |
| 4,851,000 A | 7/1989 | Gupta | |
| 4,877,661 A | 10/1989 | House et al. | |
| 4,955,899 A | 9/1990 | Della et al. | |
| 5,026,513 A | 6/1991 | House et al. | |
| 5,064,435 A | 11/1991 | Porter | |
| 5,071,609 A | 12/1991 | Tu et al. | |
| 5,123,918 A | 6/1992 | Perrier et al. | |
| 5,163,955 A | 11/1992 | Love et al. | |
| 5,415,667 A | 5/1995 | Frater | |
| 5,469,868 A | 11/1995 | Reger | |
| 5,476,589 A | 12/1995 | Bacino | |
| 5,489,297 A | 2/1996 | Duran | |
| 5,534,007 A | 7/1996 | St et al. | |
| 5,549,663 A | 8/1996 | Cottone, Jr. | |
| 5,554,183 A | 9/1996 | Nazari | |
| 5,554,185 A | 9/1996 | Block et al. | |
| 5,562,729 A | 10/1996 | Purdy | |
| 5,628,791 A | 5/1997 | Bokros et al. | |
| 5,673,102 A | 9/1997 | Suzuki et al. | |
| 5,708,044 A | 1/1998 | Branca | |
| 5,718,973 A | 2/1998 | Lewis et al. | |
| 5,749,852 A | 5/1998 | Schwab et al. | |
| 5,752,934 A | 5/1998 | Campbell et al. | |
| 5,759,192 A | 6/1998 | Saunders | |
| 5,769,884 A | 6/1998 | Solovay | |
| 5,772,884 A | 6/1998 | Tanaka et al. | |
| 5,788,626 A | 8/1998 | Thompson | |
| 5,814,405 A | 9/1998 | Branca et al. | |
| 5,824,043 A | 10/1998 | Cottone, Jr. | |
| 5,843,158 A | 12/1998 | Lenker et al. | |
| 5,843,161 A | 12/1998 | Solovay | |
| 5,843,171 A | 12/1998 | Campbell et al. | |
| 5,853,419 A | 12/1998 | Imran | |
| 5,925,061 A | 7/1999 | Ogi et al. | |
| 5,928,281 A | 7/1999 | Huynh et al. | |
| 5,935,162 A | 8/1999 | Dang | |
| 5,935,163 A | 8/1999 | Gabbay | |
| 5,944,654 A | 8/1999 | Crawford | |
| 5,957,974 A | 9/1999 | Thompson et al. | |
| 6,010,529 A | 1/2000 | Hierweck et al. | |
| 6,013,854 A | 1/2000 | Moriuchi | |
| 6,019,785 A | 2/2000 | Strecker | |
| 6,035,896 A * | 3/2000 | Liardet | A61M 15/0016 |
| | | | 137/849 |
| 6,042,588 A | 3/2000 | Munsinger et al. | |
| 6,042,605 A | 3/2000 | Martin et al. | |
| 6,042,606 A | 3/2000 | Frantzen | |
| 6,086,612 A | 7/2000 | Jansen | |
| 6,110,198 A | 8/2000 | Fogarty et al. | |
| 6,117,169 A | 9/2000 | Moe | |
| 6,129,758 A | 10/2000 | Love | |
| 6,161,399 A | 12/2000 | Jayaraman | |
| 6,165,211 A | 12/2000 | Thompson | |
| 6,171,335 B1 | 1/2001 | Wheatley et al. | |
| 6,174,329 B1 | 1/2001 | Callol et al. | |
| 6,174,331 B1 | 1/2001 | Moe et al. | |
| 6,190,406 B1 | 2/2001 | Duerig et al. | |
| 6,197,143 B1 | 3/2001 | Bodnar | |
| 6,217,609 B1 | 4/2001 | Haverkost | |
| 6,245,012 B1 | 6/2001 | Kleshinski | |
| 6,261,320 B1 | 7/2001 | Tam et al. | |
| 6,261,620 B1 | 7/2001 | Michael | |
| 6,283,994 B1 * | 9/2001 | Moe | A61F 2/2412 |
| | | | 623/2.12 |
| 6,283,995 B1 | 9/2001 | Moe et al. | |
| 6,287,334 B1 | 9/2001 | Moll et al. | |
| 6,328,763 B1 | 12/2001 | Love et al. | |
| 6,334,873 B1 | 1/2002 | Lane et al. | |
| 6,336,937 B1 | 1/2002 | Vonesh et al. | |
| 6,352,552 B1 | 3/2002 | Levinson et al. | |
| 6,379,382 B1 | 4/2002 | Yang | |
| 6,436,132 B1 | 8/2002 | Patel et al. | |
| 6,454,798 B1 | 9/2002 | Moe | |
| 6,454,799 B1 | 9/2002 | Schreck | |
| 6,461,382 B1 | 10/2002 | Cao | |
| 6,461,665 B1 | 10/2002 | Scholander | |
| 6,482,228 B1 | 11/2002 | Norred | |
| 6,488,701 B1 | 12/2002 | Nolting et al. | |
| 6,541,589 B1 | 4/2003 | Baillie | |
| 6,558,418 B2 | 5/2003 | Carpentier et al. | |
| 6,562,069 B2 | 5/2003 | Cai et al. | |
| 6,582,464 B2 | 6/2003 | Gabbay | |
| 6,613,086 B1 | 9/2003 | Moe et al. | |
| 6,620,190 B1 | 9/2003 | Colone | |
| 6,626,939 B1 | 9/2003 | Burnside et al. | |
| 6,645,244 B2 | 11/2003 | Shu et al. | |
| 6,666,885 B2 | 12/2003 | Moe | |
| 6,673,102 B1 | 1/2004 | Vonesh et al. | |
| 6,673,107 B1 | 1/2004 | Brandt et al. | |
| 6,726,715 B2 | 4/2004 | Sutherland | |
| 6,730,118 B2 | 5/2004 | Spenser et al. | |
| 6,730,120 B2 | 5/2004 | Berg et al. | |
| 6,755,856 B2 | 6/2004 | Fierens et al. | |
| 6,755,857 B2 | 6/2004 | Peterson et al. | |
| 6,758,858 B2 | 7/2004 | McCrea et al. | |
| 6,890,350 B1 | 5/2005 | Walak | |
| 6,893,460 B2 | 5/2005 | Spenser et al. | |
| 6,916,338 B2 | 7/2005 | Speziali | |
| 6,936,067 B2 | 8/2005 | Buchanan | |
| 6,953,332 B1 | 10/2005 | Kurk et al. | |
| 7,022,132 B2 | 4/2006 | Kocur | |
| 7,049,380 B1 | 5/2006 | Chang et al. | |
| 7,083,642 B2 | 8/2006 | Sirhan et al. | |
| 7,105,018 B1 | 9/2006 | Yip et al. | |
| 7,137,184 B2 | 11/2006 | Schreck | |
| 7,163,556 B2 | 1/2007 | Xie et al. | |
| 7,238,200 B2 | 7/2007 | Lee et al. | |
| 7,247,167 B2 | 7/2007 | Gabbay | |
| 7,306,729 B2 | 12/2007 | Bacino et al. | |
| 7,381,218 B2 | 6/2008 | Schreck | |
| 7,419,678 B2 | 9/2008 | Falotico | |
| 7,462,675 B2 | 12/2008 | Chang et al. | |
| 7,510,575 B2 | 3/2009 | Spenser et al. | |
| 7,513,909 B2 | 4/2009 | Lane et al. | |
| 7,531,611 B2 | 5/2009 | Sabol et al. | |
| 7,563,277 B2 | 7/2009 | Case et al. | |
| 7,708,775 B2 | 5/2010 | Rowe et al. | |
| 7,727,274 B2 | 6/2010 | Zilla et al. | |
| 7,758,640 B2 | 7/2010 | Vesely | |
| 7,780,725 B2 | 8/2010 | Haug et al. | |
| 7,789,908 B2 | 9/2010 | Sowinski et al. | |
| 7,803,186 B1 | 9/2010 | Li et al. | |
| 7,811,314 B2 | 10/2010 | Fierens et al. | |
| 7,815,763 B2 | 10/2010 | Fierens et al. | |
| 7,879,085 B2 | 2/2011 | Sowinski et al. | |
| 7,887,562 B2 | 2/2011 | Young et al. | |
| 7,914,569 B2 | 3/2011 | Nguyen et al. | |
| 7,927,364 B2 | 4/2011 | Fierens et al. | |
| 7,927,365 B2 | 4/2011 | Fierens et al. | |
| 7,935,141 B2 | 5/2011 | Randall et al. | |
| 7,967,829 B2 | 6/2011 | Gunderson et al. | |
| 7,967,853 B2 | 6/2011 | Eidenschink et al. | |
| 7,993,394 B2 | 8/2011 | Hariton et al. | |
| 8,048,440 B2 | 11/2011 | Chang et al. | |
| 8,062,359 B2 | 11/2011 | Marquez et al. | |
| 8,092,523 B2 | 1/2012 | Li et al. | |
| 8,167,935 B2 | 5/2012 | McGuckin et al. | |
| 8,226,710 B2 | 7/2012 | Nguyen et al. | |
| 8,246,678 B2 | 8/2012 | Salahieh et al. | |
| 8,252,037 B2 | 8/2012 | Styrc et al. | |
| 8,303,647 B2 | 11/2012 | Case | |

(56) References Cited

U.S. PATENT DOCUMENTS

| | | |
|---|---|---|
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |

(56) References Cited

U.S. PATENT DOCUMENTS

| | | |
|---|---|---|
| 2006/0287719 A1 | 12/2006 | Rowe et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink |
| 2008/0319531 A1 | 12/2008 | Doran et al. |
| 2009/0005854 A1 | 1/2009 | Juang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |

(56) References Cited

U.S. PATENT DOCUMENTS

| | | |
|---|---|---|
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Baccheretti et al. |
| 2016/0015422 A1 | 1/2016 | De et al. |
| 2016/0074161 A1 | 3/2016 | Bennett |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0276014 A1 | 9/2020 | Burkart et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0257369 A1 | 8/2022 | Burkart et al. |
| 2022/0273426 A1 | 9/2022 | Hagaman et al. |
| 2022/0378575 A1 | 12/2022 | Busalacchi et al. |

FOREIGN PATENT DOCUMENTS

| | | |
|---|---|---|
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |

(56) References Cited

FOREIGN PATENT DOCUMENTS

| | | |
|---|---|---|
| EP | 2255750 A2 | 12/2010 |
| EP | 2400923 A1 | 1/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| FR | 2591100 A1 | 6/1987 |
| GB | 2312485 A | 10/1997 |
| GB | 2513194 A | 10/2014 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2007-525291 A | 9/2007 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-543399 A | 12/2013 |
| JP | 2014-513585 A | 6/2014 |
| JP | 2014-517720 A | 7/2014 |
| JP | 2016-501104 A | 1/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/084595 A1 | 9/2005 |
| WO | 2005/112827 A2 | 12/2005 |
| WO | 2006/019626 A1 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A2 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A1 | 1/2014 |
| WO | 2014/018432 A2 | 1/2014 |
| WO | 2014/099150 A1 | 6/2014 |
| WO | 2014/099163 A1 | 6/2014 |
| WO | 2014/099722 A1 | 6/2014 |
| WO | 2014/144937 A2 | 9/2014 |
| WO | 2015/045002 A1 | 4/2015 |
| WO | 2015/085138 A1 | 6/2015 |
| WO | 2015/171743 A2 | 11/2015 |
| WO | 2015/173794 A1 | 11/2015 |
| WO | 2016/028591 A1 | 2/2016 |
| WO | 2016/044223 A1 | 3/2016 |
| WO | 2016/100913 A1 | 6/2016 |
| WO | 2016/172349 A1 | 10/2016 |
| WO | 2016/186909 A1 | 11/2016 |
| WO | 2017/038145 A1 | 3/2017 |
| WO | 2017/096157 A1 | 6/2017 |
| WO | 2019/067219 A1 | 4/2019 |
| WO | 2019/067220 A1 | 4/2019 |
| WO | 2019/074607 A1 | 4/2019 |

(56) References Cited

FOREIGN PATENT DOCUMENTS

| WO | 2019/074869 A1 | 4/2019 |
| WO | 2019/089138 A1 | 5/2019 |
| WO | 2019/246268 A1 | 12/2019 |

OTHER PUBLICATIONS

Opposition from EP16196687.4, mailed on Dec. 12, 2019, 38 pages.
Opposition from EP17187595.8, filed Sep. 12, 2019, 50 pages.
International Preliminary Report on Patentability received for PCT Patent Application No. PCT/US2018/050768, dated May 14, 2020, 8 pages.
International Preliminary Report on Patentability received for PCT Patent Application No. PCT/US2018/050786, dated Apr. 23, 2020, 9 pages.
Cardiac Surgery in the Adult, Third Edition, Chapter 2 2008.
EPO Form 1002 for EP16196687.4 Filed Dec. 28, 2016.
Forward citations for E12 obtained from: https://scholar.google.com/scholar?cites=5981833429320176658&assdt=2005&sciodt=0,5&hl=en.
International Search Report and Written Opinion received for PCT Application No. PCT/US2020/020550, dated Jun. 9, 2020, 12 pages.
Google Image Search Results, "S-Shaped", accessed Nov. 1, 2013.
International Preliminary Report on Patentability received for PCT Patent Application No. PCT/US15/50113, dated Mar. 30, 2017, 9 pages.
International Preliminary Report on Patentability received for PCT Patent Application No. PCT/US2020/027921, dated Oct. 21, 2021, 11 pages.
International Preliminary Report on Patentability received for PCT Patent Application No. PCT/US2020/044603, dated Feb. 10, 2022, 9 pages.
International Search Report and Written Opinion received for PCT Patent Application No. PCT/US2020/044603, dated Oct. 20, 2020, 12 pages.
International Search Report and Written Opinion received for PCT Patent Application No. PCT/US2020/027921, dated Jul. 24, 2020, 16 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.

* cited by examiner

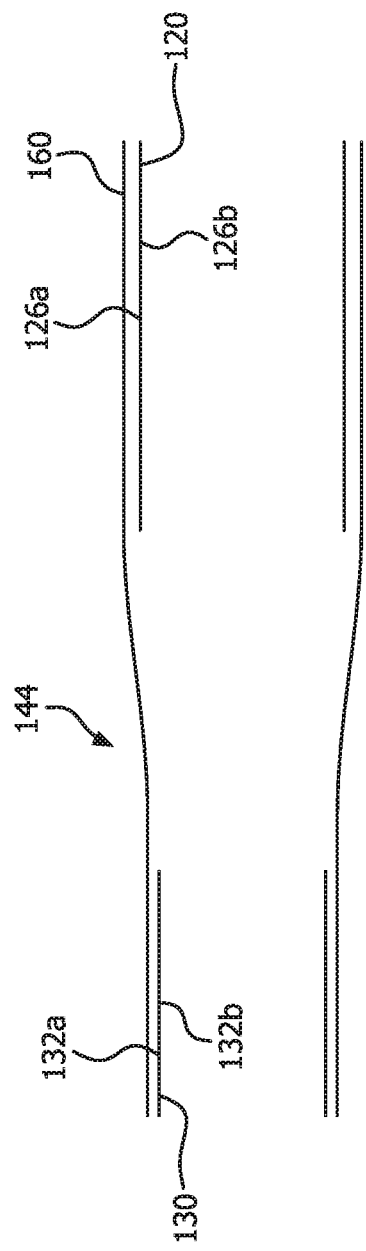
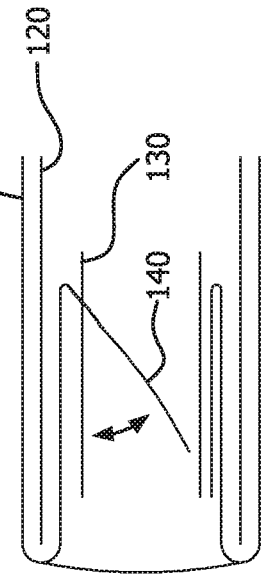
FIG. 5A
FIG. 5B

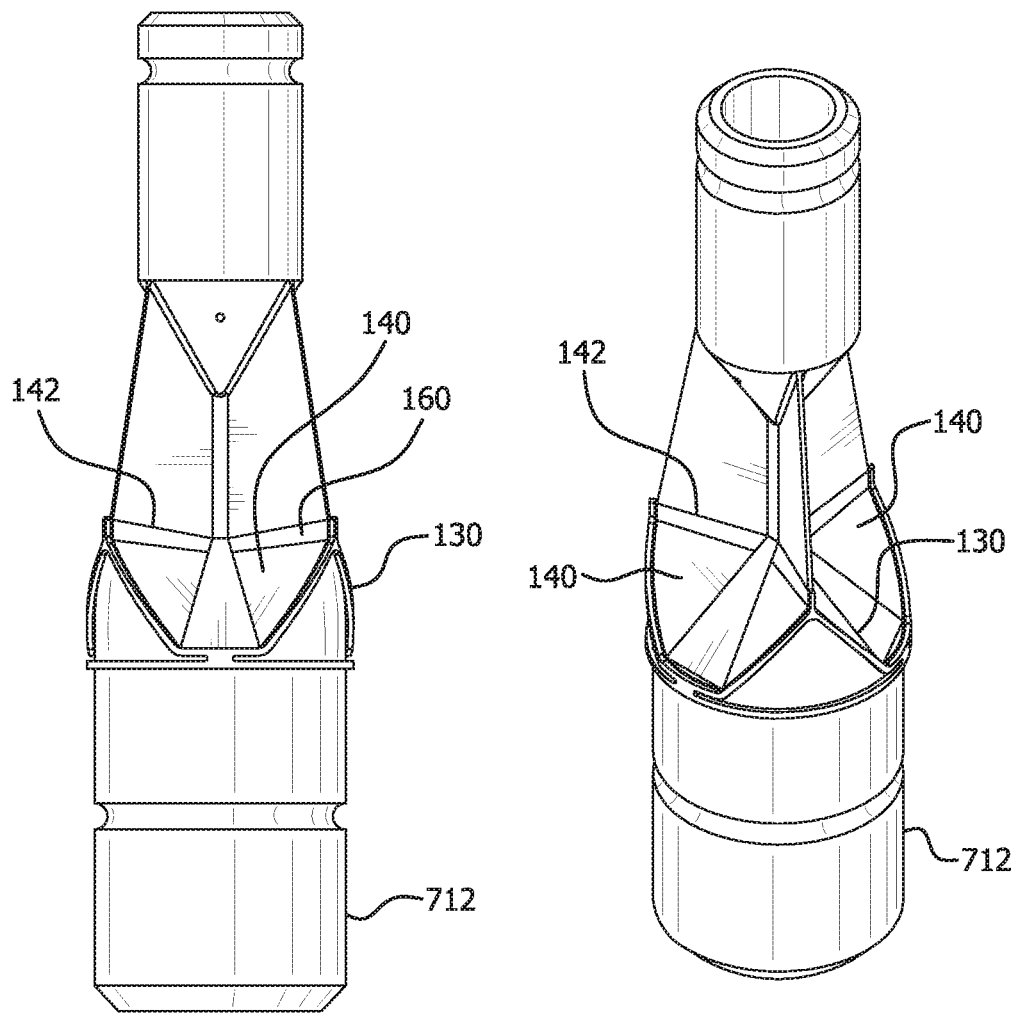

METHODS FOR IMPROVED PROSTHETIC HEART VALVE WITH LEAFLET SHELVING

CROSS-REFERENCE TO RELATED APPLICATION

This application is a continuation of U.S. patent application Ser. No. 15/720,441, filed Sep. 29, 2017, which is a continuation of U.S. patent application Ser. No. 14/792,380, filed Jul. 6, 2015, now U.S. Pat. No. 9,827,089, issued Nov. 28, 2017, which is a divisional of U.S. patent application Ser. No. 13/869,878, filed Apr. 24, 2013, now U.S. Pat. No. 9,101,469, issued Aug. 11, 2015, which claims priority to Provisional Application 61/739,721, filed Dec. 19, 2012, all of which are incorporated herein by reference in their entireties for all purposes.

FIELD

The present disclosure relates generally to prosthetic valves and more specifically to synthetic flexible leaflet-type prosthetic valve devices, systems, and methods with controlled leaflet opening.

BACKGROUND

The durability of synthetic valve leaflets is partially a function of the character of bending by the leaflet during the opening-closing cycle. Small radius bends, creases and intersecting creases, can produce high stress zones in the leaflet. These high stress zones can cause the formation of holes and tears under repetitive loading.

Prosthetic valves may be delivered using surgical or transcatheter techniques. A surgical valve is implanted into a patient using open-heart surgical techniques. The surgical valve is usually manufactured to have a fixed diameter as opposed to a transcatheter valve which is required to attain a range of diameters for access and delivery. The surgical valve is usually provided with a sewing cuff about a perimeter of the valve to allow for suturing to the native tissue orifice. Sewing cuffs are well known in the art.

In addition to the valve durability issues discussed above, the transcatheter valve must also be able to withstand the handling and deployment stresses associated with being compressed and expanded The shape most often described as preferable is modeled after the native human aortic valve. Though nature dictates the optimum shape for the native tissues to form a heart valve, we have discovered this is not true for synthetic materials; accordingly, the design specified in the current disclosure is instead intended to place the synthetic material under a minimized stress condition as compared to those based on copies of the native valve. This is partially accomplished through reduced buckling in the leaflet material.

There exists a need for a durable synthetic prosthetic valve that may be delivered either surgically or endovascularly.

SUMMARY

Described embodiments are directed to an apparatus, system, and methods for valve replacement, such as cardiac valve replacement. More specifically, described embodiments are directed toward flexible leaflet valve devices in which the base of each leaflet forms a straight line.

A prosthetic valve is provided comprising a leaflet frame and a plurality of leaflets coupled to the leaflet frame. Each leaflet includes a free edge and a leaflet base. Each leaflet has a planar zone in a central region, wherein the planar zone is substantially planar. The planar zone defines a shape having an area, wherein the area is larger nearer the base than the free edge. The leaflet is operable to bend about a straight base segment of the leaflet base in which the planar zone base of the planar zone of the leaflet is a straight line that has a length of less than C.

A method of forming a prosthetic heart valve, comprises: providing a leaflet frame having a generally tubular shape, the leaflet frame defining a plurality of leaflet windows wherein each of the leaflet windows includes two leaflet window sides, a leaflet window base, and a leaflet window top; providing a film; wrapping the film about the leaflet frame bringing more than one layer of the film into contact with additional layers of the film defining at least one leaflet extending from each of the leaflet windows; and bonding the layers of film to itself and to the leaflet frame, wherein each leaflet has substantially a shape of an isosceles trapezoid having two leaflet sides, a leaflet base and a free edge opposite the leaflet base, wherein the two leaflet sides diverge from the leaflet base, wherein the leaflet base is substantially flat, wherein the leaflet base is coupled to the window base and wherein each of the two leaflet sides are coupled to one of the two window sides providing a generally annular support structure, each leaflet having a planar zone in a central region, wherein the planar zone is substantially planar, wherein the planar zone defines a shape having an area, wherein the area is larger nearer the base than the free edge, wherein the leaflet is operable to bend about a straight base segment of the leaflet base in which the planar zone base of the planar zone of the leaflet is a straight line that has a length of less than C.

In some embodiments, particularly in the case of transcatheter valves, the leaflet frame is placed coaxially within an outer frame. In these embodiments the leaflet frame and the outer frame act in concert as the diameter is reduced for delivery, and then re-expanded at the recipient site.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 5A is a cross-sectional view of an embodiment of the valve during manufacture;

FIG. 5B is a cross-sectional view of an embodiment of the valve;

FIG. 13A is a side view of the leaflet frame on a cutting mandrel, in accordance with an embodiment;

FIG. 13B is a perspective view of the leaflet frame on the cutting mandrel of FIG. 13A.

DETAILED DESCRIPTION

Figure 1A:
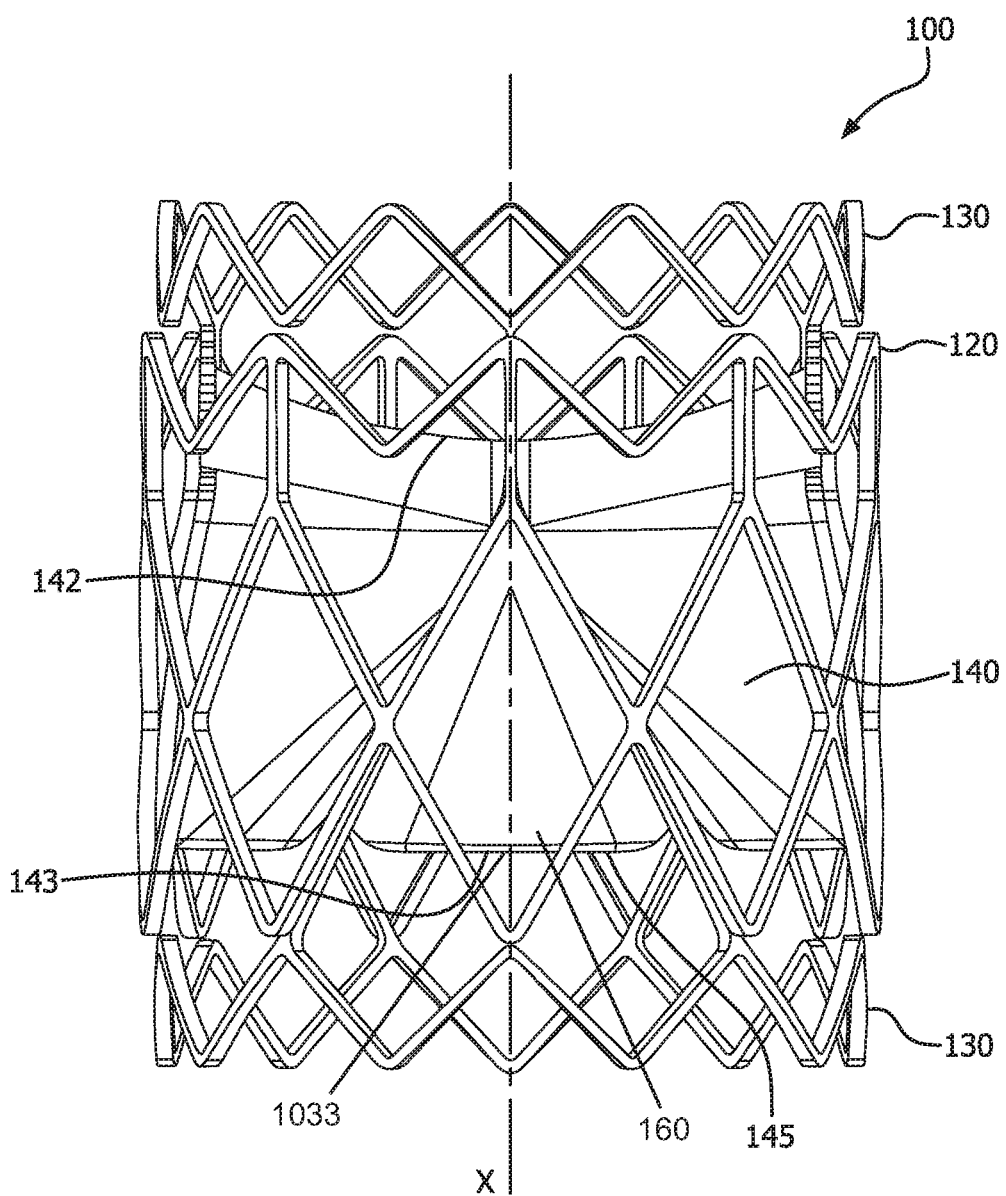
FIG. 1A is a side view of an embodiment of a valve.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets opens and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to a film or a biological material, such as, but not limited to, bovine pericardium.

The term leaflet window is defined as that space that a frame defines from which a leaflet extends. The leaflet may extend from frame elements or adjacent to frame elements and spaced apart therefrom.

The terms native valve orifice and tissue orifice refer to an anatomical structure into which a prosthetic valve may be placed. Such anatomical structure includes, but is not limited to, a location wherein a cardiac valve may or may not have been surgically removed. It is understood that other anatomical structures that may receive a prosthetic valve include, but are not limited to, veins, arteries, ducts and shunts. Although reference is made herein to replacing a native valve with a prosthetic valve, it is understood and appreciated that a valve orifice or implant site may also refer to a location in a synthetic or biological conduit that may receive a valve for a particular purpose, and therefore the scope of the embodiments provided herein is not limited to valve replacement.

As used herein, "couple" means to join, connect, attach, adhere, affix, or bond, whether directly or indirectly, and whether permanently or temporarily.

Embodiments herein include various apparatus, systems, and methods for a prosthetic valve suitable for surgical and transcatheter placement, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

Embodiments provided herein are related to controlled leaflet opening. The durability of the valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading.

Controlled bending is of particular importance in thin, high-modulus synthetic leaflets, since the bending in these materials tends to be cellophane-like. If the leaflet bending character is uncontrolled, not only do creases form, but crease intersections lead to formation of large three dimensional structures that oppose bending and slow down the leaflet motion, both in opening and closing: in order to avoid this, the sequence of opening of the parts of the leaflet must be controlled.

In accordance with some embodiments presented herein, a prosthetic valve comprises two frames; a leaflet frame and an outer frame. The film that comprises the leaflet may be coupled to the inner surface of the leaflet frame. In some other embodiments, the film that comprises the leaflet is contained between the leaflet frame and the outer frame and extends through a leaflet window defined by the leaflet frame. The leaflet, therefore, is significantly prevented from peeling or delaminating as it is contained between the leaflet frame and outer frame, as compared to where the leaflets are only coupled to the inner surface of the leaflet frame.

In accordance with some embodiments presented herein, a prosthetic valve comprises two frames; a leaflet frame and an outer frame. The leaflet frame and the outer frame are separated from each other by a film. In other words, there is a metal to polymer to metal interconnection, wherein there is no metal to metal contact between the two frames.

In accordance with some embodiments presented herein, a prosthetic valve comprises two frames; a leaflet frame and an outer frame. The leaflet frame is nested within the outer frame, wherein the leaflet frame and outer frame cooperate to provide relatively high resistance to flat plate compression, among other things. In accordance with some embodiments, the outer frame provides frame elements that overlay the leaflet windows that are defined by the leaflet frame so as to provide structural support over the leaflet windows. In accordance with some embodiments, the outer frame provides frame elements that overlay the leaflet windows that are defined by the leaflet frame so as to prevent tissue from extending into the leaflet windows when implanted. In accordance with some embodiments, the outer frame provides frame elements that overlay the leaflet windows that are defined by the leaflet frame and act in concert so as to allow the frame assembly to compress and expand uniformly for transcatheter embodiments.

In accordance with some embodiments presented herein, a prosthetic valve comprises two frames; a leaflet frame and an outer frame. The leaflet frame defines leaflet windows that define, in part, the shape of the leaflets. In some embodiments the leaflet comprises a flat base, wherein the leaflet bends from the base towards the free edge with minimal creasing and fluttering. In accordance with embodiments, the leaflet comprises a flat base, that, among other things, provides for one or more of a shorter valve length, substantially prevents blood stagnation and pooling and encourages washing at the base, as compared to leaflets having a rounded base.

In accordance with some embodiments presented herein, a prosthetic valve comprises two frames; a leaflet frame and an outer frame. The leaflet frame defines leaflet windows from which the leaflets extend. The leaflets are defined by the intersection of films that form an overlapping zone so as to define, at least in part, the leaflet base and/or the leaflet sides.

Embodiments provided herein address controlled leaflet opening. The durability of the valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading. Embodiments provided herein provide a feature of leaflet shape so as to minimize crease formation, which is of particular importance in thin, high-modulus leaflets, since the bending in these materials tends to be cellophane-like. If the leaflet bending is unrestricted, not only do creases form, but crease intersections lead to formation of large three dimensional structures that oppose bending and slow down the leaflet motion, both in opening and closing.

Valve

Figure 14A:
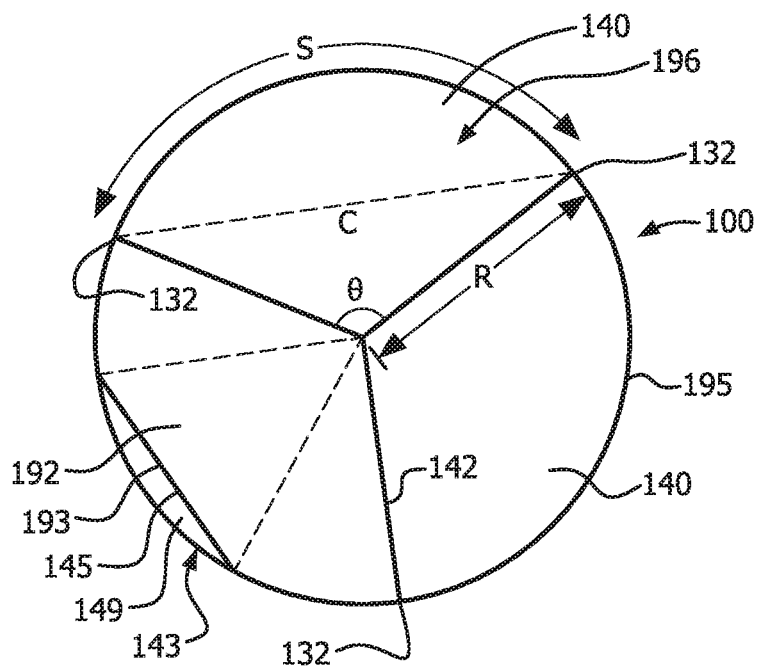
FIGS. 14A and 14B are simplified top view representations of a heart valve having three leaflets, in closed and open positions, respectively.
Figure 14B:
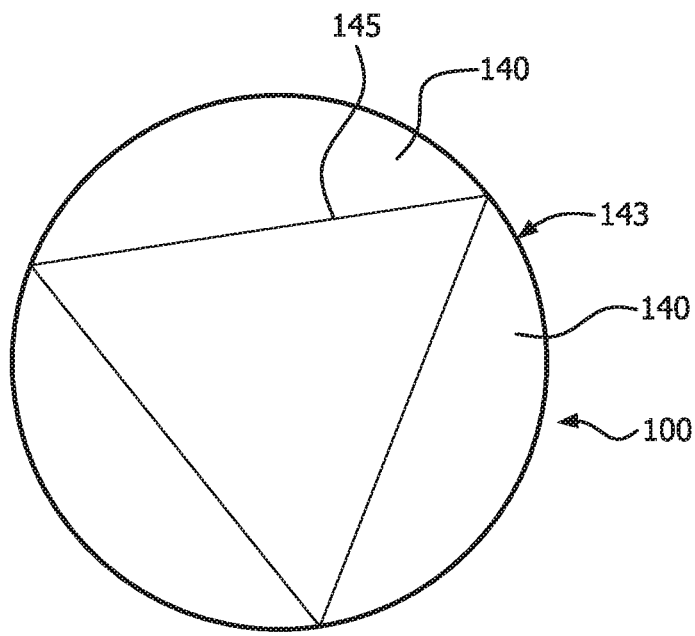

FIGS. 14A and 14B are simplified top view representations of a valve 100 having three leaflets 140, in closed and open positions, respectively. The leaflets 140 have a free edge 142 and a leaflet base 143. The leaflet base 143 is defined, at least in part, by where the leaflet 140 bends when it is open.

Figure 3A:
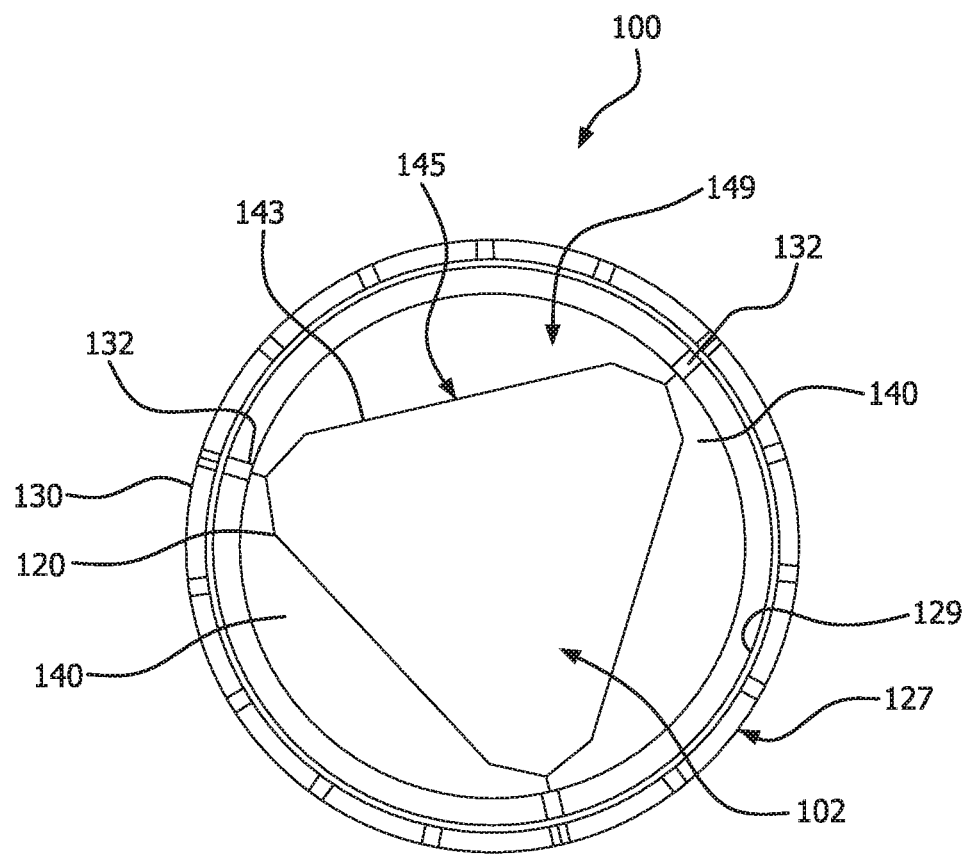
FIG. 3A is an axial or top view of the embodiment of the valve of FIG. 1A in an open configuration.

In any trileaflet valve 100, each leaflet 140 occupies a segment 196 of a circle 195 defined by a leaflet frame 130, as shown in FIG. 3A. The valve 100 is symmetric so that angle θ is 120° and arc length S is ⅓ of the diameter of the circle 195.

In certain configurations bending of the leaflet 140 may occur along chord C. Chord C is defined as a straight line that extends from two commissure posts 132. Leaflet actuation in this case is rapid, but the total flow area is restricted to a small equilateral triangle with sides of length R providing less than optimal flow area leading to excessive restriction.

In certain other configurations, bending of the leaflet 140 may occur along arc length S, at least for high-modulus, thin materials, if bending of the leaflet base 143 occurs close to the leaflet frame 130 essentially along the circle 195. In such cases the closing action of the leaflet 140 is delayed when flow is reversed.

In accordance with embodiments provided herein, for optimum performance of the leaflet 140, it is appreciated herein that bending of the leaflet 140 adjacent the leaflet base 143 must be along a substantially straight line instead of an arc, but this straight line has a length that must be less than a length of chord C. This straight line is represented by a straight base segment 145 in FIG. 14A.

In embodiments of prosthetic valves 100 provided herein, each of the leaflets 140 comprises a leaflet base 143 having a flat portion 149 that defines a shelf structure, as shown in FIG. 14A. In operation, the leaflet 140 bends from the flat portion 149 along the straight base segment 145 of the leaflet base 143 towards the free edge 142 with minimal creasing and fluttering. The leaflet base 143 having a flat portion 149 provides, among other things, a shorter valve length, substantially prevents blood stagnation and pooling and encourages washing at the leaflet base 143, as compared to leaflets 140 having a rounded leaflet base 143. A leaflet base 143 that has a straight base segment 145 also provides a superior hemodynamic outcome during the closing phase of the valve.

In accordance with embodiments of the prosthetic valve 100 provided herein, a planar zone 192 of the leaflet 140 comprises a planar zone base 193 which is coincident with the straight base segment 145 which is a substantially straight line that has a length that is less than a length of chord C. This combination produces basal bending of the leaflet 140.

Figure 1B:
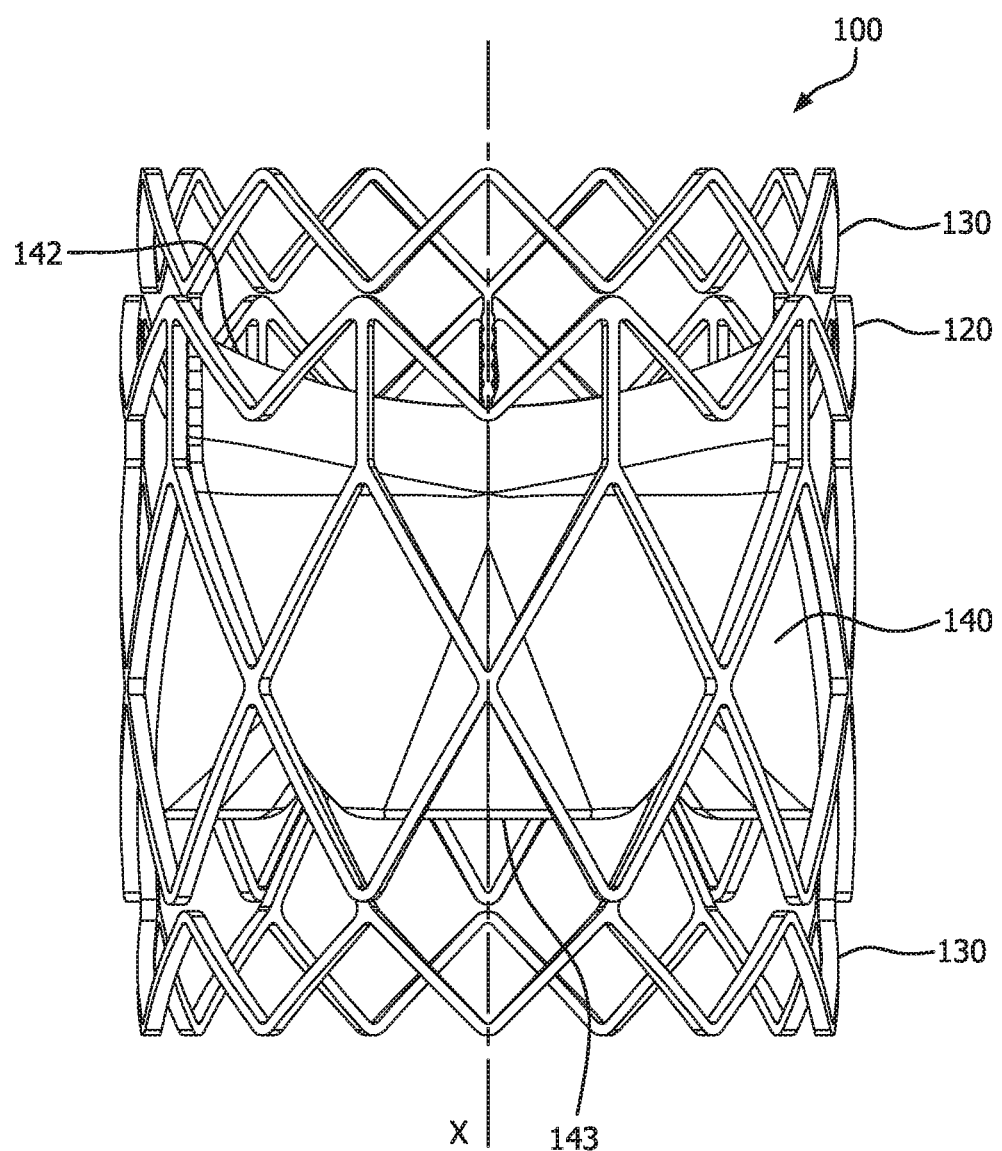
FIG. 1B is a side view of the embodiment of the valve of FIG. 1A.
Figure 1C:
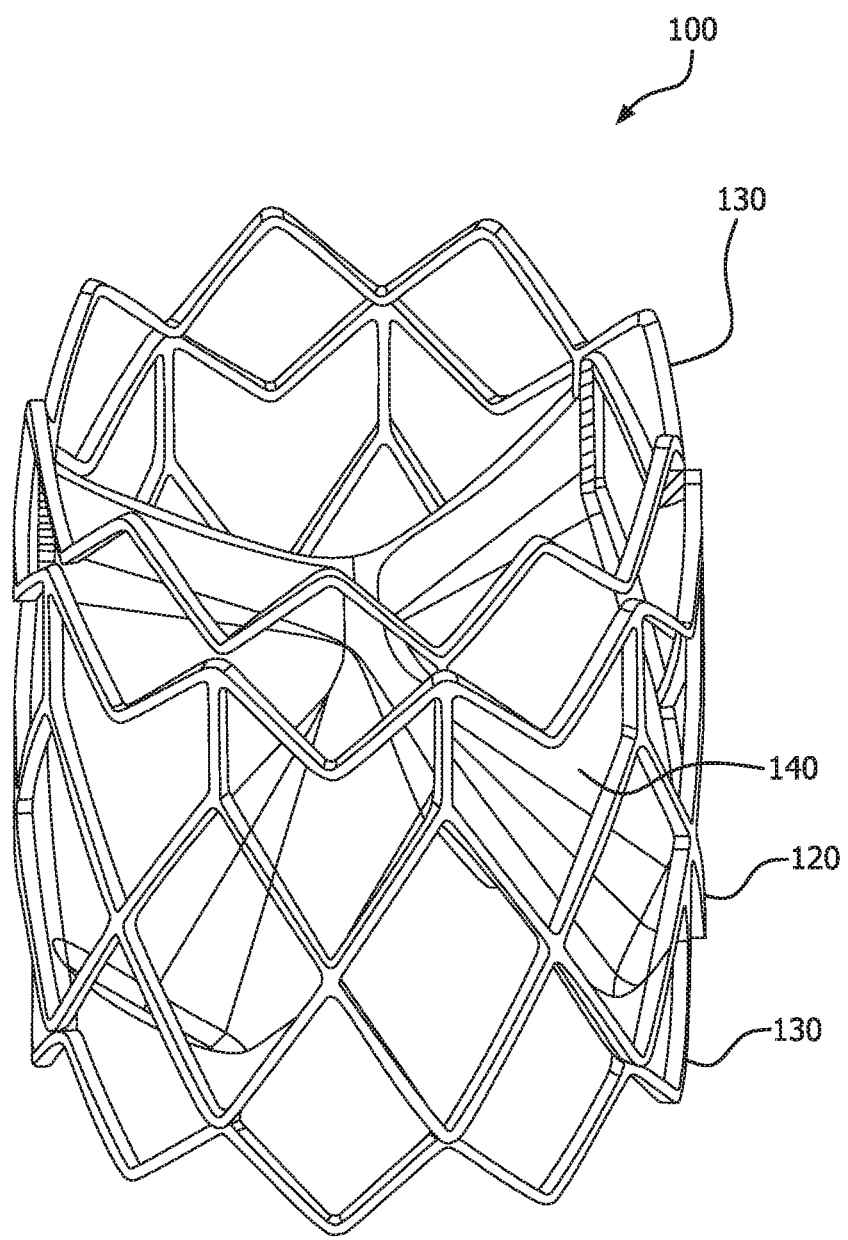
FIG. 1C is a perspective view of the embodiment of the valve of FIG. 1A.
Figure 3B:
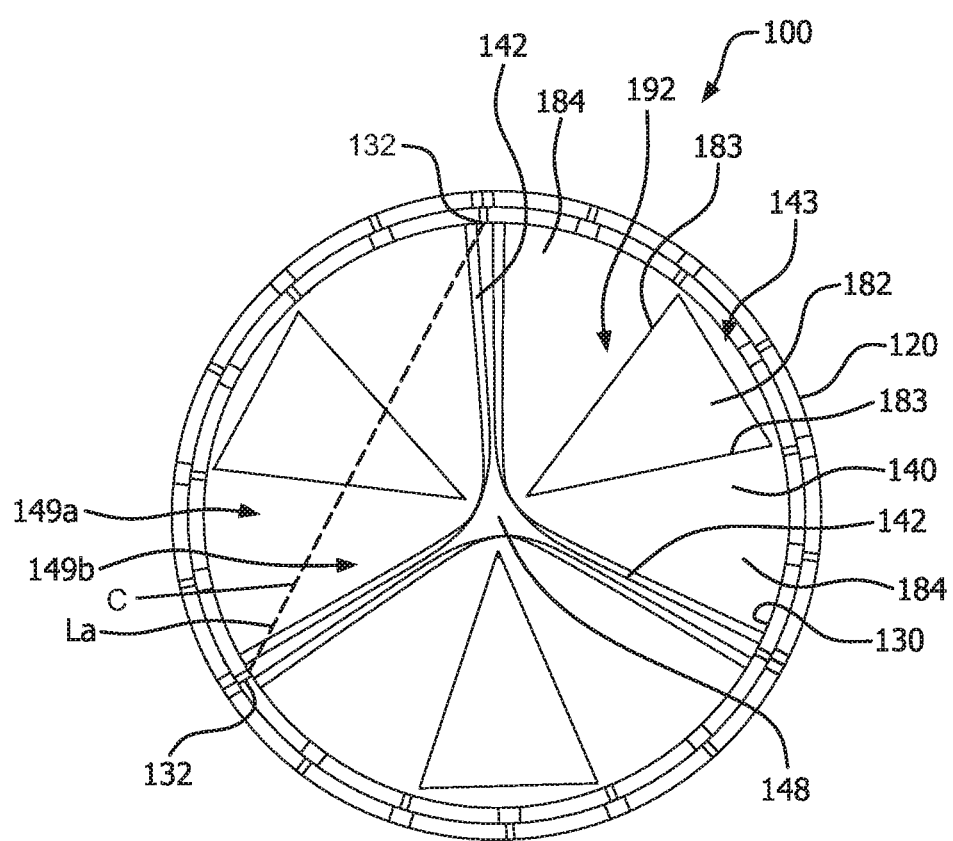
FIG. 3B is an axial or top view of the embodiment of the valve of FIG. 1A in a closed configuration.
Figure 11A:
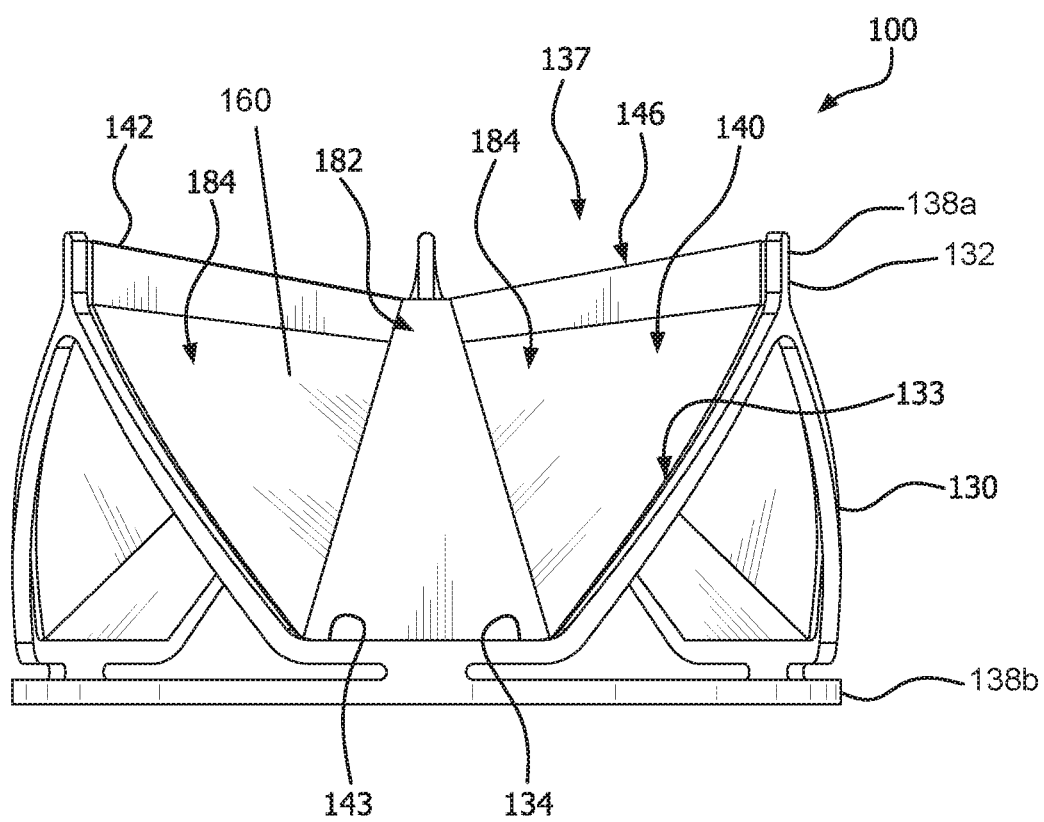
FIG. 11A is a side view of an embodiment of a valve.
Figure 11B:
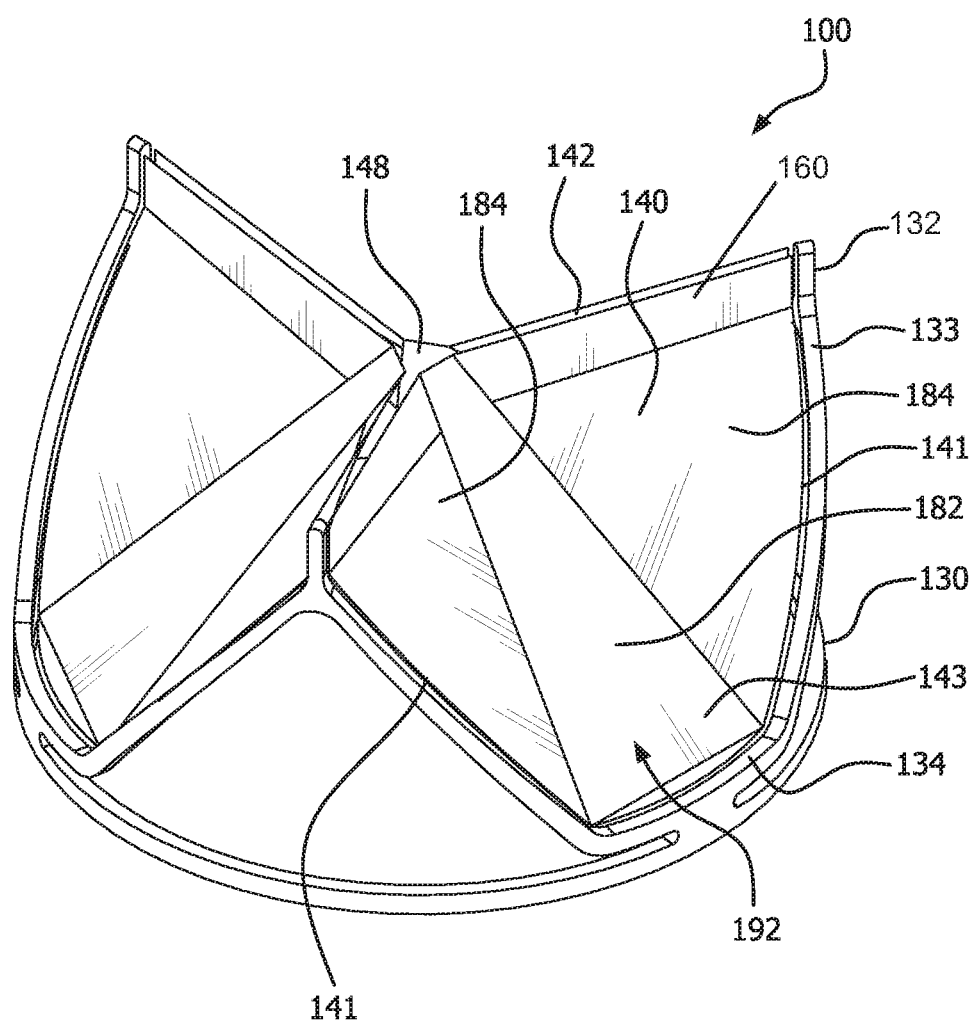
FIG. 11B is a top view of the embodiment of the valve of FIG. 1A.

FIG. 1A is a side view of a valve 100, in accordance with an embodiment. FIG. 1B is also a side view of the valve 100 of FIG. 1A rotated 60 degrees about the longitudinal axis X. FIG. 1C is a perspective view of the valve 100 of FIG. 1A. FIG. 11A is a side view of another embodiment of a valve 100. FIG. 11B is a perspective view of the embodiment of the valve of FIG. 11A. FIGS. 3A and 3B are axial views of the valve 100 of FIG. 1A, in an open and closed configuration, respectively, which presents a configuration substantially the same as for the valve 100 of the embodiment of FIG. 11A. It is shown that bending of the leaflet 140 occurs at the leaflet base 143, a portion of which is along a straight base segment 145. In FIGS. 1C, 3B and 11B, the leaflets 140 are shown slightly open to better show the features but it is understood that a fully closed valve 100 will have the free edges 142 of the leaflets 140 coming together to coapt under the influence of downstream fluid pressure which results in closing the valve to prevent downstream blood from flowing retrograde through the valve.

Figure 2A:
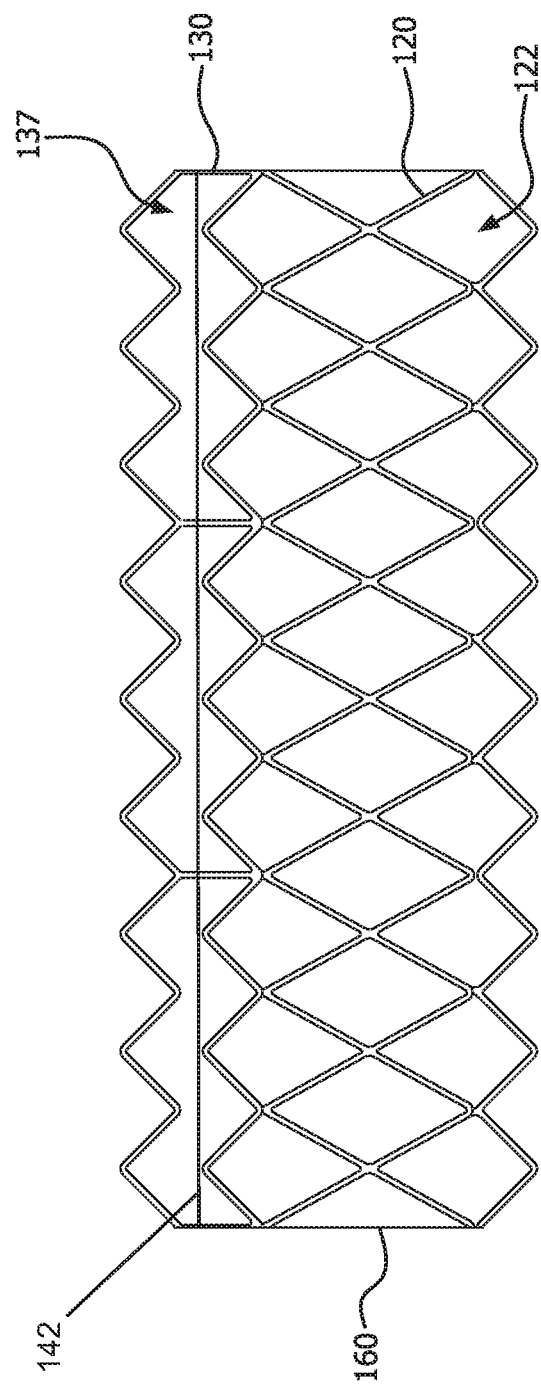
FIG. 2A is a representation of the embodiment of the valve of FIG. 1A unrolled to a flat orientation.
Figure 2B:
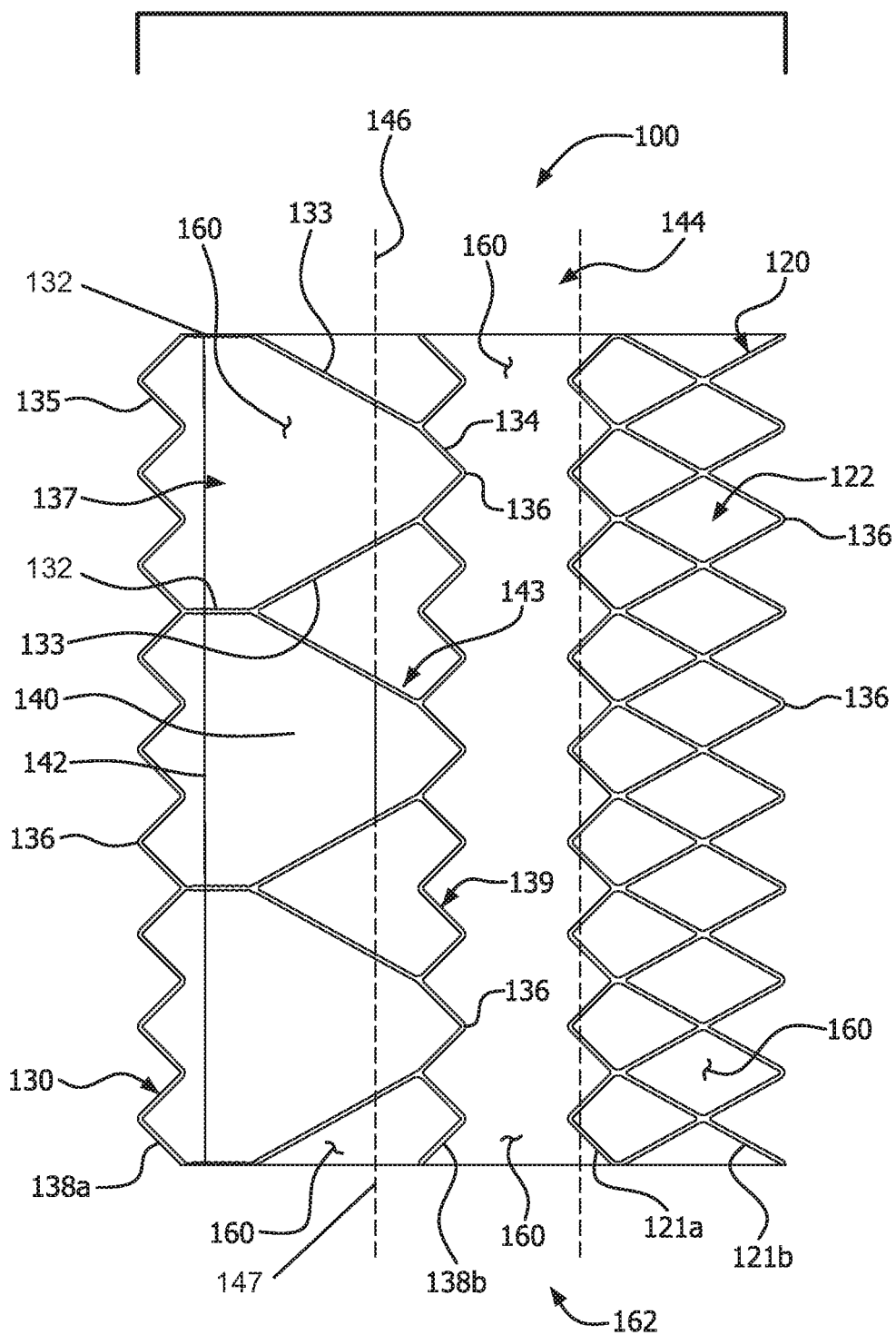
FIG. 2B is an exploded representation of the embodiment of the valve of FIG. 1A unrolled to a flat orientation.

FIG. 1A is a side view of a valve 100, in accordance with an embodiment. FIG. 1B is also a side view of the valve 100 of FIG. 1A rotated 60 degrees about the longitudinal axis X. FIG. 1C is a perspective view of the valve 100 of FIG. 1A. FIG. 2A is a side view of the valve 100 of FIG. 1A wherein the valve 100 has been longitudinally cut and laid open to better illustrate the elements of the generally tubular-shaped valve 100. FIG. 2B is an exploded view of the embodiment of FIG. 2A. FIGS. 3A and 3B are axial views of the valve 100 of FIG. 1A in an open and closed configuration, respectively. The valve 100 of the embodiment of FIG. 1A is suitable for surgical or transcatheter delivery and deployment. As will be explained below, the valve 100 is operable to be reduced in diameter for transcatheter delivery and radially expanded for deployment.

Referring again to the embodiment of the valve 100 of FIG. 1A, the valve 100 comprises an outer frame 120, a leaflet frame 130, and a film 160 covering the outer frame 120 and leaflet frame 130, coupling the outer frame 120 to the leaflet frame 130, and defining leaflets 140. The embodiment of valve 100 is discussed further related to a transcatheter valve that may be compressed and re-expanded. It is understood that the embodiment of valve 100 is also applicable to a surgical valve by the addition of a sewing cuff 171 as shown in FIG. 4B. Leaflet frame and outer frame configurations related to surgical valve only embodiments where the valves have a fixed diameter, will be discussed in other embodiments later in this disclosure.

FIG. 11A is a side view of another embodiment of a valve 100. FIG. 11B is a perspective view of the embodiment of the valve of FIG. 11A. The valve 100 of the embodiment of FIG. 11A is suitable for surgical placement. As will be explained below, the valve 100 is operable to retain a predetermined diameter that resists radial compression or expansion. Referring again to the embodiment of the valve 100 of FIG. 11A, the valve 100 comprises a leaflet frame 130, and a film 160 covering the leaflet frame 130 and defining leaflets 140.

The embodiments of the valve 100 of FIGS. 1A and 11A are provided as non-limiting examples to show that the concepts presented herein related to leaflets with straight line basal bending about a straight base segment of the leaflet in which the planar zone base of the planar zone of the leaflet is a line of length less than chord C, may be applied to prosthetic heart valves of many configurations and designs.

Outer Frame

The embodiment of the valve 100 of FIG. 1A comprises a leaflet frame 130 and an outer frame 120. The outer frame 120 is a generally tubular member defining a generally open pattern of apertures 122, in accordance with an embodiment. In accordance with transcatheter embodiments, the outer frame 120 is operable to allow the outer frame 120 to be compressed and expanded between different diameters. The outer frame 120 comprises an outer frame first end 121*a* and an outer frame second end 121*b* opposite the outer frame first end 121*a*. The outer frame 120 comprises an outer frame outer surface 126*a* and an outer frame inner surface 126*b* opposite the outer frame outer surface 126*a*, as shown in FIG. 5A. The outer frame 120 may comprise a structure known in the art as a stent. A stent is a tubular member that may have a small diameter suitable for percutaneous transcatheter delivery into the anatomy, and may be expanded to a larger diameter when deployed into the anatomy. Stents having various designs and material properties are well known in the art.

Figure 1D:
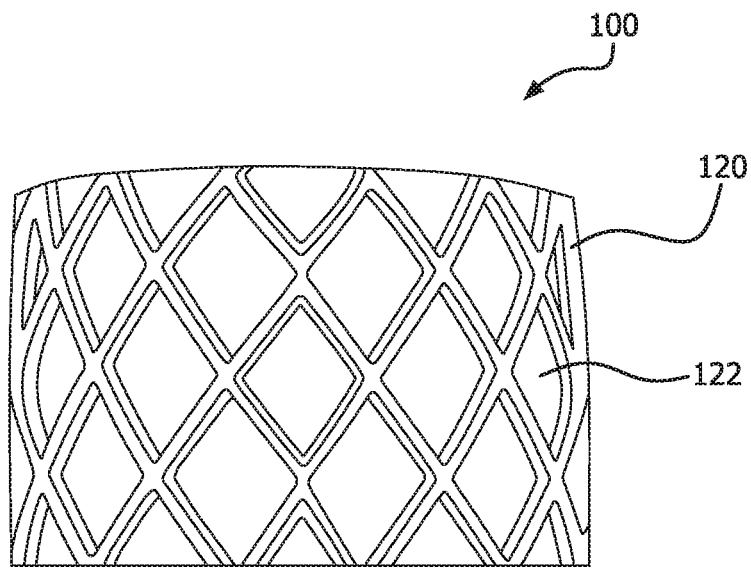
FIG. 1D is a representation of a valve in an expanded configuration.

By way of example, and as illustrated in the embodiments of FIGS. 1A-1C and 2A-2B, the valve 100 includes the outer frame 120 that defines a stent having apertures 122 having generally a diamond shape when in a large diameter configuration, as shown generally in FIG. 1D. Upon compression to a smaller diameter, the apertures 122 deform to generally define an elongated diamond shape, as shown generally in FIG. 1E. Upon re-expansion to a larger diameter, the apertures 122 re-expand to again define a generally diamond shape.

Figure 6A:
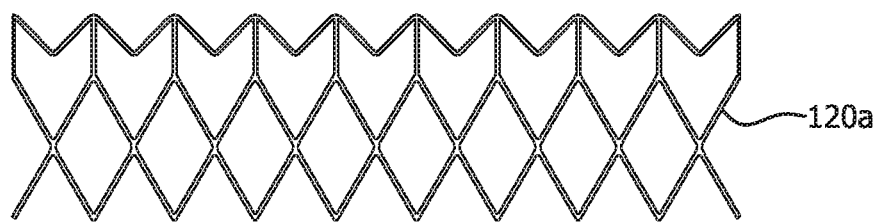
FIG. 6A is a representation of an embodiment of an outer frame unrolled to a flat orientation.
Figure 6B:
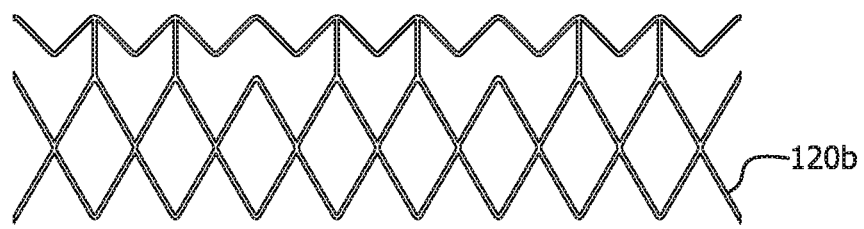
FIG. 6B is a representation of an embodiment of an outer frame unrolled to a flat orientation.

FIGS. 6A and 6B are side views of alternative embodiments of the outer frame 120*a*, 120*b* wherein the outer frame has been longitudinally cut and laid open to better illustrate the elements of the outer frame. It is appreciated that there are many embodiments of the outer frame having configurations suitable for the particular purpose.

An open framework of the stent can define any number of features, repeatable or otherwise, such as geometric shapes and/or linear or meandering series of sinusoids. Geometric shapes can comprise any shape that facilitates substantially uniform circumferential compression and expansion. The outer frame 120 may comprise a cut tube, or any other element suitable for the particular purpose. The outer frame 120 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

It is known that stents of various designs may be elastically deformable so as to be self-expanding under spring loads. It is also known that stents of various designs may be plastically deformable so as to be mechanically expanded such as with a balloon. It is also known that stents of various designs may be plastically deformable as well as elastically deformable. The embodiments of the outer frame 120 presented herein are not to be limited to a specific stent design or mode of expansion.

The outer frame 120 can comprise any metallic or polymeric biocompatible material. For example, the outer frame 120 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Figure 4A:
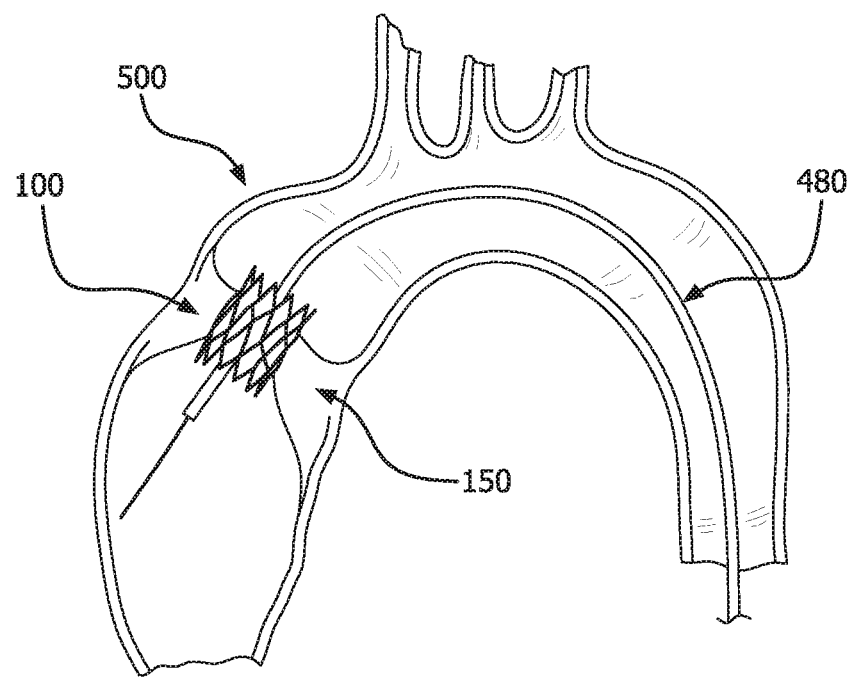
FIG. 4A is a side view of an embodiment of a transcatheter delivery system within anatomy.
Figure 4B:
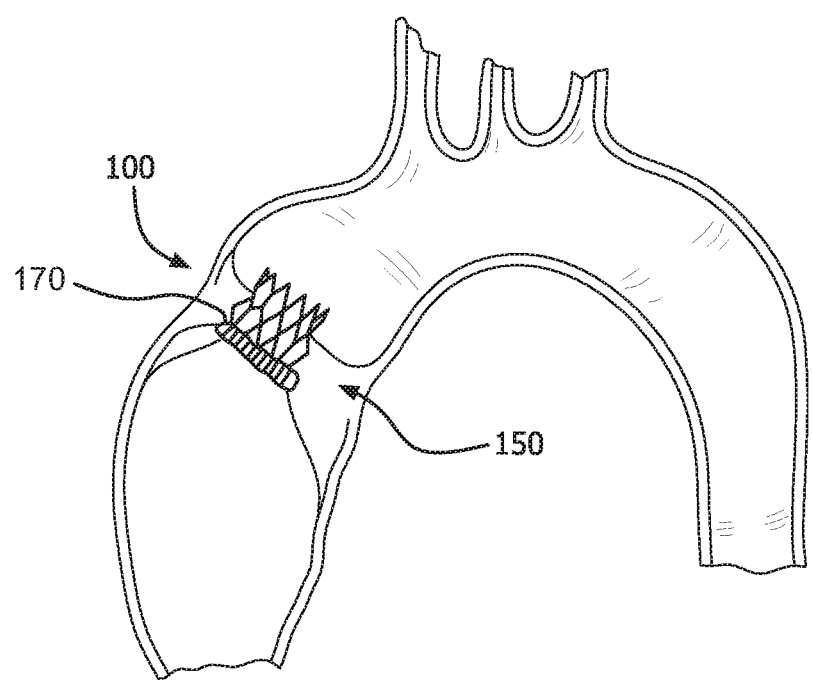
FIG. 4B is a side view of an embodiment of a surgical valve within anatomy.

In accordance with embodiments, the outer frame 120 and/or leaflet frame 130 can be configured to provide positive engagement with an implant site to firmly anchor the valve 100 to the site, as shown in FIG. 4A representing a transcatheter deployment of the valve 100. In accordance with an embodiment, the outer frame 120 can comprise a sufficiently rigid frame having small elastic recoil so as to maintain sufficient apposition against a tissue orifice 150 to maintain position. In accordance with another embodiment, the outer frame 120 and/or leaflet frame 130 can be configured to expand to a diameter that is larger than a tissue orifice 150 so that when valve 100 expands into the tissue orifice 150, it can be firmly seated therein. In accordance with another embodiment, the outer frame 120 can comprise one or more anchors (not shown) configured to engage the implant site, such as a tissue orifice 150, to secure the valve 100 to the implant site.

It is appreciated that other elements or means for coupling the valve 100 to an implant site are anticipated. By way of example, but not limited thereto, other means, such as mechanical and adhesive means may be used to couple the valve 100 to a synthetic or biological conduit.

Sewing Cuff

In accordance with a surgical valve 100 embodiment, the valve 100 further comprises a sewing cuff 171 about an outer frame outer surface 127 in accordance with an embodiment, as shown in FIG. 4B, or about the leaflet frame 130 in embodiments where there is not outer frame 120. The sewing cuff 171 is operable to provide structure that receives suture for coupling to the implant site. The sewing cuff 171 may comprise any suitable material, such as, but not limited to, double velour polyester. The sewing cuff 171 may be located circumferentially around a perimeter of the outer frame 120 or the leaflet frame 130 if there is no outer frame 120. Sewing cuffs 171 are known in the art.

Leaflet Frame

Referring again to FIGS. 1C and 2B, the leaflet frame 130 of the embodiment of FIG. 1C, is a generally tubular member defining a plurality of leaflet windows 137 coupled together by connecting elements 139, in accordance with an embodiment. The leaflet frame 130 comprises a leaflet frame first end 138*a* and a leaflet frame second end 138*b* opposite the leaflet frame first end 138*a*. The leaflet frame 130 comprises a leaflet frame outer surface 132*a* and a leaflet frame inner surface 132*b* opposite the leaflet frame outer surface 132*a*, as shown in FIG. 5A. The leaflet frame first end 138*a* and the leaflet frame second end 138*b* define a generally zigzag configuration to facilitate flexion about flex points 136 such as which facilitates compression and expansion between different diameters for compression onto a delivery device and expansion by a balloon for the transcatheter valve 100 embodiments, as generally explained for the outer frame 120. As will be discussed later, the surgical valve 100 embodiment may or may not have the zigzag configuration since the surgical valve 100 may be of a fixed diameter and need not be operable to compress and re-expand.

The leaflet frame 130 may be referred to in a general sense as a stent or a frame.

The leaflet frame 130 defines a predetermined repeating pattern as shown in FIG. 2B, in accordance with an embodiment. The leaflet frame 130 defines three interconnected leaflet windows 137 having a substantially triangular shape. Each of the leaflet windows 137 includes two leaflet window sides 133 including commissure posts 132, a leaflet window base 134, and a leaflet window top 135. In this embodiment, the leaflet window base 134 defines a flex point 136 which will be described further below. A leaflet window side 133 and leaflet window top 135 of one leaflet window 137 is interconnected with a leaflet window side 133 of an adjacent leaflet window 137 at the commissure posts 132.

The leaflet frame 130 defines any number of features and geometric shapes that facilitate substantially uniform circumferential compression and expansion. The leaflet frame 130 may comprise a cut tube, or any other element suitable for the particular purpose. The leaflet frame 130 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

The leaflet frame 130 can comprise any metallic or polymeric biocompatible material. For example, the leaflet frame 130 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

As will be described in more detail below, a film 160 is disposed over each of the three leaflet windows 137 to form a leaflet 140. Further embodiments will be described below wherein the leaflet window 137 defines shapes other than a substantially triangular shape, including, but not limited to a parabolic shape and a trapezoidal shape, with and without a leaflet window top 135, suitable for a particular purpose of an embodiment of a surgical and transcatheter valve 100.

Figure 7A:
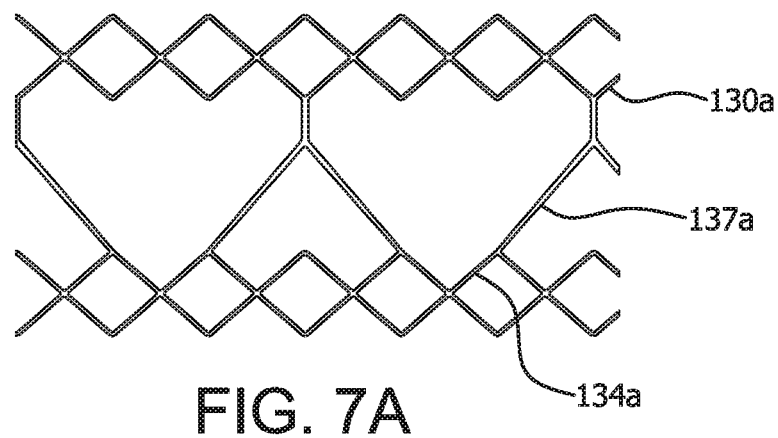
FIG. 7A is a representation of an embodiment of a leaflet frame unrolled to a flat orientation.
Figure 7B:
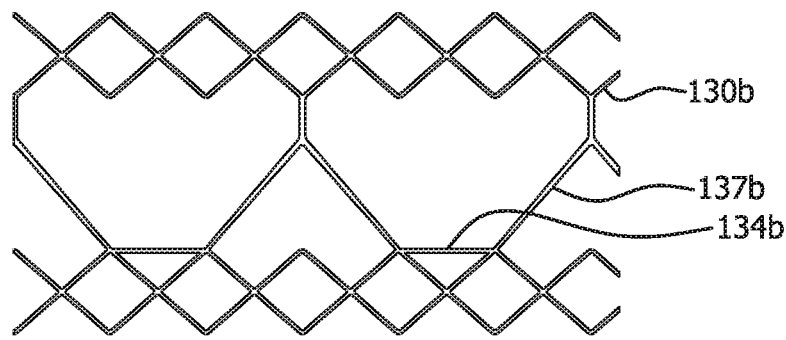
FIG. 7B is a representation of an embodiment of a leaflet frame unrolled to a flat orientation.

FIGS. 7A and 7B are side views of alternative embodiments of the leaflet frame 130*a*, 130*b* wherein the leaflet frame has been longitudinally cut and laid open to better illustrate the elements of the leaflet frame. The leaflet frame 130*a* includes leaflet windows 137*a* having a substantially triangular shape defining a pointed leaflet window base 134*a*. The leaflet frame 130*b* includes leaflet windows 137*b* having a substantially triangular shape defining a flat leaflet window base 134*b*. The flat leaflet window base 134*b* may be used to define the leaflet base.

Figure 8A:
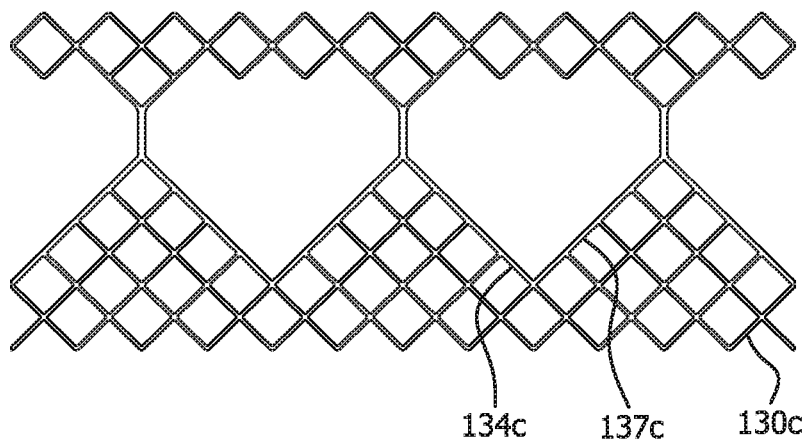
FIG. 8A is a representation of an embodiment of a leaflet frame unrolled to a flat orientation.
Figure 8B:
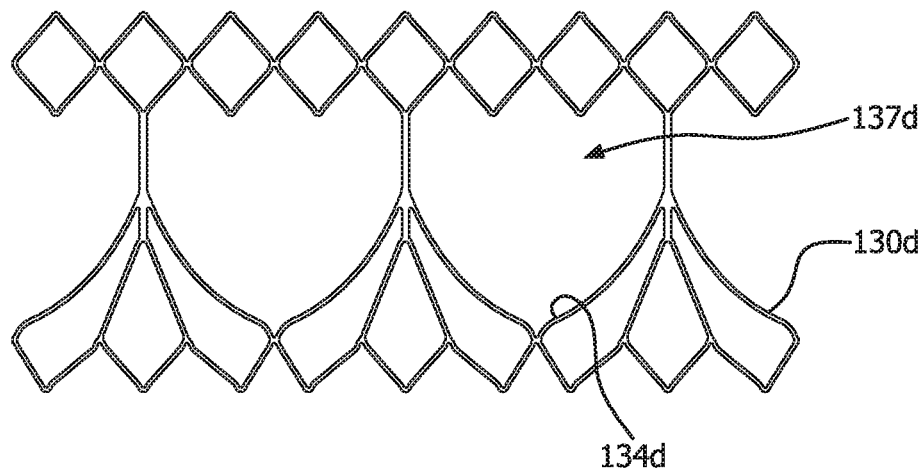
FIG. 8B is a representation of an embodiment of a leaflet frame unrolled to a flat orientation.
Figure 8C:
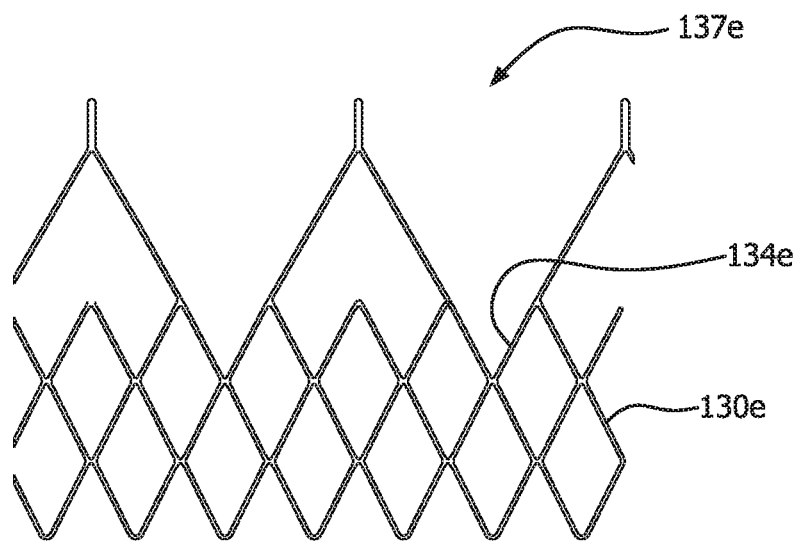
FIG. 8C is a representation of an embodiment of a leaflet frame unrolled to a flat orientation.

FIGS. 8A-8C are side views of alternative embodiments of the leaflet frame 130*c*-130*e* wherein the leaflet frame has been longitudinally cut and laid open to better illustrate the elements of the leaflet frame. The leaflet frame 130*c* includes leaflet windows 137*c* having a substantially triangular shape defining a pointed leaflet window base 134*c*. The leaflet frame 130*d* includes leaflet windows 137*d* having a substantially parabolic shape defining a rounded leaflet window base 134*d*. The flat leaflet window base 134*b* may be used to define the leaflet base. The leaflet frame 130*e* includes leaflet windows 137e having a substantially triangular shape defining a pointed leaflet window base 134e but not having a leaflet window top.

Figure 8D:
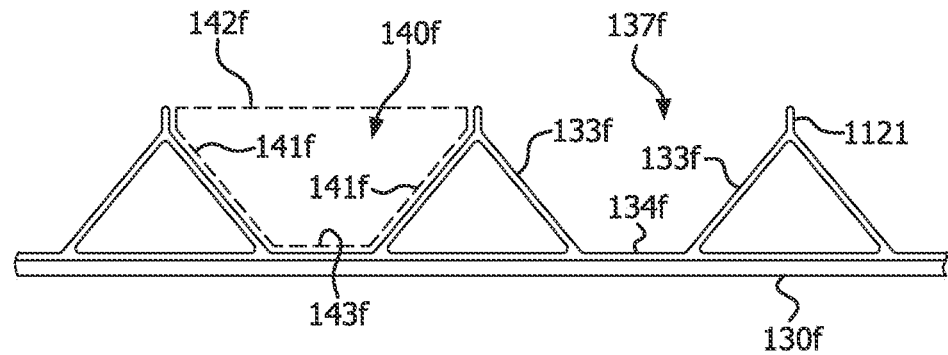
FIG. 8D is a representation of an embodiment of a leaflet frame unrolled to a flat orientation.

FIG. 8D is a side view of an alternative embodiment of the leaflet frame 130f wherein the leaflet frame 130f has been longitudinally cut and laid open to better illustrate the elements of the leaflet frame. The leaflet frame 130f includes leaflet windows 137f having a substantially isosceles trapezoid shape defining a flat leaflet window base 134f. The flat leaflet window base 134f may be used to define the leaflet base. A leaflet 140f is shown in dashed line to represent where the leaflet 143f is located within the leaflet window 137f, the leaflet window 137f being defined by the leaflet window sides 133f and the leaflet window base 134f. In accordance with other embodiments of the prosthetic valve, each leaflet 140f has substantially the shape of an isosceles trapezoid having two leaflet sides 141f, a leaflet base 143f and a free edge 142f opposite the leaflet base 143f, wherein the two leaflet sides 141f diverge from the leaflet base 143f, wherein the leaflet base 143f is substantially flat, as shown in dashed lines in FIG. 8D. The leaflet frame 130f further comprises extension elements 1121 that may be used to provide additional coaptation of the leaflet free edges.

Figure 8E:
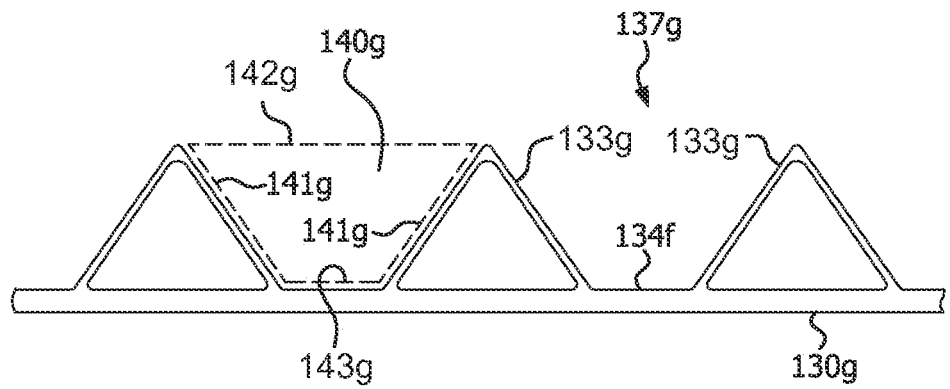
FIG. 8E is a representation of an embodiment of a leaflet frame unrolled to a flat orientation.

FIG. 8E is a side view of an alternative embodiment of the leaflet frame 130g wherein the leaflet frame 130g has been longitudinally cut and laid open to better illustrate the elements of the leaflet frame. The leaflet frame 130g includes leaflet windows 137g having a substantially isosceles trapezoid shape defining a flat leaflet window base 134f. The flat leaflet window base 134g may be used to define the leaflet base. A leaflet 140g is shown in dashed line to represent where the leaflet 140g is located within the leaflet window 137g. In accordance with other embodiments of the prosthetic valve, each leaflet 140g has substantially the shape of an isosceles trapezoid having two leaflet sides 141g, a leaflet base 142g and a free edge 143g opposite the leaflet base, wherein the two leaflet sides 141g diverge from the leaflet base 143f, wherein the leaflet base 143f is substantially flat, as shown in dashed lines in FIG. 8E.

Figure 8F:
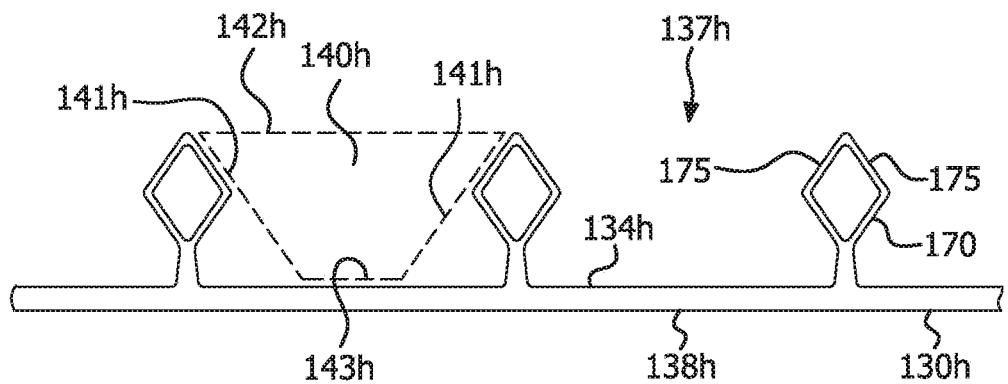
FIG. 8F is a representation of an embodiment of a leaflet frame unrolled to a flat orientation.

FIG. 8F is a side view of an alternative embodiment of the leaflet frame 130h wherein the leaflet frame 130h has been longitudinally cut and laid open to better illustrate the elements of the leaflet frame 130h. The leaflet frame 130h comprises a base element 138h and a plurality of spaced apart spade elements 170 interconnected by the base element 138h. Each leaflet window 137h is defined by a spade side 175 of one spade element 170 and a side 175 of an adjacent spade element 170, and wherein each leaflet window base 134h is defined by the base element 138h. In accordance with an embodiment of the prosthetic valve, each leaflet 140h has substantially the shape of an isosceles trapezoid having two leaflet sides 141h, a leaflet base 142h and a free edge 143h opposite the leaflet base 142h, wherein the two leaflet sides 141h diverge from the leaflet base 142h, wherein the leaflet base 142h is substantially flat, as shown in dashed lines in FIG. 8F. It is noted that at least a portion of the leaflet side 141h is supported by the leaflet frame 130h at the spade side 175 and at least a portion of the leaflet side 141h between the spade side 175 and the leaflet window base 134h is not supported by the leaflet frame 130h.

As previously discussed, the leaflet window base may be used to define the leaflet base in accordance with embodiments. Also as previously discussed, the leaflet base may be defined as a virtual leaflet base 1033 by a fold line 147 in the film 160 spaced apart from the leaflet window base 134, as shown in FIG. 2B. It is appreciated that there are many embodiments of the outer frame 120 having configurations suitable for the particular purpose.

In valve 100 embodiments suitable for transcatheter placement, the leaflet frame 130 is elastically, plastically, or both, compressible to obtain a relatively small diameter to accommodate percutaneous transcatheter mounting and delivery. In accordance with an embodiment as shown in FIG. 2B, the leaflet frame 130 may comprise one or more flex points 136 so as to provide a preferential flexing location for the leaflet frame 130 to flex when compressed to a smaller diameter. A flex point 136 comprises a site on the leaflet frame 130 that undergoes the highest degree of bending when transitioning from an expanded state to collapsed state and vice versa. The flex point 136 can comprise a geometry, structural modification or material modification, among others, that biases the leaflet frame 130 to bend at the flex point 136 when compressed.

The leaflet frame 130 may comprise, such as, but not limited to, any elastically deformable metallic or polymeric biocompatible material, in accordance with embodiments. The leaflet frame 130 may comprise a shape-memory material, such as nitinol, a nickel-titanium alloy. Other materials suitable for the leaflet frame 130 include, but are not limited to, other titanium alloys, stainless steel, cobalt-nickel alloy, polypropylene, acetyl homopolymer, acetyl copolymer, other alloys or polymers, or any other biocompatible material having adequate physical and mechanical properties to function as a leaflet frame 130 as described herein.

In accordance with an embodiment, the leaflet frame 130 and the outer frame 120 comprise a shape memory material operable to flex under load and retain its original shape when the load is removed, thus allowing the leaflet frame 130 and the outer frame 120 to self-expand from a compressed shape to a predetermined shape. The leaflet frame 130 and the outer frame 120 may comprise the same or different materials. In accordance with an embodiment, the leaflet frame 130 and the outer frame 120 are plastically deformable to be expanded by a balloon. In another embodiment the outer frame 120 and the leaflet frame 130 are elastically deformable so as to be self-expanding.

Film

The film 160 is generally any sheet-like material that is biologically compatible and configured to couple to the outer frame 120 and the leaflet frame 130, in accordance with embodiments. It is understood that the term "film" is used generically for one or more biocompatible materials suitable for a particular purpose. The leaflets 140 are also comprised of the film 160.

In accordance with an embodiment, the biocompatible material is a film 160 that is not of a biological source and that is sufficiently flexible and strong for the particular purpose, such as a biocompatible polymer. In an embodiment, the film 160 comprises a biocompatible polymer that is combined with an elastomer, referred to as a composite.

It is also understood that the film 160 coupled to the outer frame 120 may not be the same film 160 coupled to the leaflet frame 130, in accordance with embodiments. Details of various types of film 160 are discussed below. In an embodiment, the film 160 may be formed from a generally tubular material to at least partially cover the outer frame 120 and the leaflet frame 130. The film 160 can comprise one or more of a membrane, composite material, or laminate. Details of various types of film 160 are discussed below.

In an embodiment, the film 160 comprises a biocompatible polymer that is combined with an elastomer, referred to as a composite. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

In another embodiment, the expanded fluoropolymer membrane has a microstructure of substantially only fibrils, as is generally taught by U.S. Pat. No. 7,306,729, to Bacino. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5 \times 10^5$ $MPa^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 µm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 µm and a mass per area of about 4.1 $g/m^2$.

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium that may be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang et al.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones(organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Leaflet

Each leaflet window 137 is provided with a biocompatible material, such as a film 160, which is coupled to a portion of the leaflet window sides 133 with the film 160 defining a leaflet 140. Each leaflet 140 defines a free edge 142 and a leaflet base 143, in accordance with an embodiment. As will be described below, it is anticipated that a plurality of embodiments of leaflet base configurations may be provided. In accordance with an embodiment, the film 160 is coupled to a portion of the leaflet window sides 133 and to the leaflet window base 134 where the leaflet 140 is defined by the portion of the leaflet window sides 133 and to the leaflet window base 134. In accordance with another embodiment, the film 160 is coupled to a portion of the leaflet window sides 133 but not the leaflet window base 134 of the leaflet frame 130 where the leaflet 140 is defined by the portion of the leaflet window sides 133 and to a virtual leaflet base 1033 defined in a fold region as will be described below.

The shape of the leaflets 140 are defined in part by the shape of the leaflet window 137 and the free edge 142. As will be discussed below in accordance with an embodiment, the shape of the leaflets 140 also depends in part on a process that induces a fold at the fold line 147 to define a virtual leaflet base 1033 as will be described further below, so as to impart a predetermined shape to the leaflet 140. Since high bending stresses are located at the leaflet base, defining a virtual leaflet base 1033 that is not bound by the leaflet window base 134 may reduce the chance of tearing of the leaflet 140 at the leaflet base 143—leaflet window base 134 interface. It may also reduce blood pooling and stagnation at the leaflet base as compared with a rounded leaflet base.

In accordance with an embodiment, substantially the entire leaflet frame 130 lies adjacent to the outer frame inner surface 129, as shown in FIG. 3A. As such, when the leaflets 140 are in a fully open position, the valve 100 presents a substantially circular valve orifice 102 as shown in FIG. 3A. Fluid flow is permitted through the valve orifice 102 when the leaflets 140 are in an open position.

As the leaflets 140 cycle between the open and closed positions, the leaflets 140 generally flex about the leaflet base 143 and the portion of the leaflet window sides 133 to which the leaflet are coupled. When the valve 100 is closed, generally about half of each free edge 142 abuts an adjacent half of a free edge 142 of an adjacent leaflet 140, as shown in FIG. 3B. The three leaflets 140 of the embodiment of FIG. 3B meet at a triple point 148. The valve orifice 102 is occluded when the leaflets 140 are in the closed position stopping fluid flow.

Referring to FIG. 3B, in accordance with an embodiment, each leaflet 140 includes a central region 182 and two side regions 184 on opposite sides of the central region 182. The central region 182 is defined by a shape substantially that of an isosceles triangle defined by two central region sides 183, the leaflet base 143 and the free edge 142. The two central region sides 183 converge from the leaflet base 143 to the free edge 142. Each of the side regions 184 have a shape substantially that of a triangle and each are defined by one of the central region sides 183, one of the leaflet sides 141, and the free edge 142.

In accordance with an embodiment, each of the two side regions 184 and the central region 182 are substantially planar when the valve 100 is in the closed position.

The leaflet 140 can be configured to actuate at a pressure differential in the blood caused, for example, by the contraction of a ventricle or atrium of the heart, such pressure differential typically resulting from a fluid pressure building up on one side of the valve 100 when closed. As the pressure on an inflow side of the valve 100 rises above the pressure on the outflow side of the valve 100, the leaflet 140 opens and blood flows therethrough. As blood flows through the valve 100 into a neighboring chamber or blood vessel, the pressure equalizes. As the pressure on the outflow side of the valve 100 rises above the blood pressure on the inflow side of the valve 100, the leaflet 140 returns to the closed position generally preventing the retrograde flow of blood through the inflow side of the valve 100.

It is understood that the leaflet frame 130 may comprise any number of leaflet windows 137, and thus leaflets 140, suitable for a particular purpose, in accordance with embodiments. Leaflet frames 130 comprising one, two, three or more leaflet windows 137 and corresponding leaflets 140 are anticipated.

In accordance with embodiments, and referring to FIGS. 3B and 11A, the central region 182 is substantially planar, defining a planar zone, when the valve 100 is in the closed position and not under fluid pressure. The planar zone has a shape substantially of an isosceles triangle with apices extending to the leaflet frame 130. Referring to FIG. 1D, an apex line La is indicated connecting the apices 147 of the leaflets 140. The apex line La divides the leaflet 140 into a first region 149*a* adjacent the leaflet frame 130, and a second region 149*b* adjacent the free edge 142. The first region 149*a* contains a larger proportion of planar zone 192 than the second region 149*b*. In other embodiments, the majority of the planar zone 192 of each leaflet 140 is located inferior and exterior to apex line La joining the apices of two adjacent commissure posts 132. The ratio of area of the planar zone 192 distributed in the first region 149*a* and second region 149*b* has been found produce better leaflet opening dynamics than if there were more area of the planar zone 192 distributed in the second region 149*b* than the first region 149*a*.

As shown in the exploded unwrapped view of FIG. 2B of the embodiment of FIG. 2A, the outer frame 120 is located substantially coplanar, laterally adjacent to and spaced apart from the leaflet frame 130. The leaflet window base 134 of the leaflet window 137 is located proximate to an outer frame first end 121*a* of the outer frame 120 with the leaflet frame first end 138*a* of the leaflet frame 130 extending away from the outer frame 120. This placement is also used in the manufacture of the valve 100 as will be discussed below. While in this placement, the film 160 is coupled to the outer frame 120 and a portion of the leaflet frame 130 which couples the outer frame 120 to the leaflet frame 130.

The film 160 that spans the space between the outer frame 120 and the leaflet frame 130 defines at least in part a fold region 144. As will be discussed further below, in accordance with an embodiment, the fold region 144 is provided to allow the leaflet frame 130 to be telescopically disposed within the outer frame 120, the outer frame 120 having an inner diameter that is larger than the outer diameter of the leaflet frame 130, in accordance with an embodiment of a method of making the valve 100, hence creating a fold within the fold region 144 along a generally circumferential line 146.

It is anticipated that the film 160 may be coupled to the leaflet frame 130 and the outer frame 120 in many ways suitable for a particular purpose, in accordance with embodiments. In accordance with an embodiment, the outer frame 120 may be wrapped with overlapping layers of a film 160 having a first composition. The leaflet frame 130 may be wrapped with overlapping layers of a film 160 having a second composition. The wrapped leaflet frame 130, the wrapped outer frame 120, and the space between the outer frame 120 and the leaflet frame 130 may be wrapped with overlapping layers of a film 160 having a third composition defining, at least in part, the fold region 144.

In another embodiment, the film 160 may be coupled to the inner or outer surface of the leaflet frame 130 and outer frame 120. In another embodiment, the film 160 may be coupled to the inner and outer surface of the leaflet frame 130 and outer frame 120 sandwiching the leaflet frame 130 and outer frame 120 between the film 160. As will be discussed below, coupling the film 160 to at least the leaflet frame outer surface 132a and the outer frame inner surface 126b, as shown in FIGS. 5A-5B may provide additional support to the leaflet 140 to prevent disengagement of the leaflet 140 from the leaflet frame 130 since a portion of the film 160 is contained between the leaflet frame 130 and the outer frame 120, as shown in FIG. 5B.

Wherever the film 160 is present it prevents blood from traveling through or across the valve 100 other than through the valve orifice 102 when the leaflets 140 are in an open position and uncovered portions of the leaflet frame 130 or outer frame 120. As such, the film 160 creates a barrier to blood flow in any interstitial space(s) or apertures 122 of the outer frame 120 and leaflet frame 130, and therebetween, that the film 160 covers.

The film 160 is fixedly secured or otherwise coupled at a single or a plurality of locations of the inner surface or outer surface of the outer frame 120 and leaflet frame 130, for example, using one or more of taping, heat shrinking, adhesion and other processes known in the art. In some embodiments, a plurality of membrane/composite layers, i.e., a laminate, are used and can be coupled to both the inner and outer surfaces of the outer frame 120 and the leaflet frame 130 to form at least a portion of the film 160.

The film 160 comprises any material(s) that have the suitable physical and mechanical properties to perform the functions described herein. The film 160 may comprise the same material that the leaflet 140 comprises or a different material. Similarly, the film 160 may or may not be homogenous in material composition. Different portions of the film 160 can comprise different materials which can give it different physical and mechanical properties.

As previously discussed, in an embodiment of a method of making the valve 100, the leaflet frame 130 is disposed within the outer frame 120 in a telescoping manner whereby folding the film 160 in the fold region 144, as shown in FIGS. 5A-5B. The leaflet frame 130 is therefore nested within the outer frame 120 while remaining coaxial therewith. The assembly is further processed to couple the fold region 144 to itself and to the wrapped leaflet frame 130 and outer frame 120 while preventing the film 160 defining the leaflets 140 from adhering to unintended parts of the valve 100 that would prevent leaflet function.

In accordance with another embodiment, the frame members defining the apertures of the leaflet frame 130 and outer frame 120 are preferentially aligned to provide overlapping and complimentary arrangement so as to proved structural rigidity to the assembly.

Figure 1E:
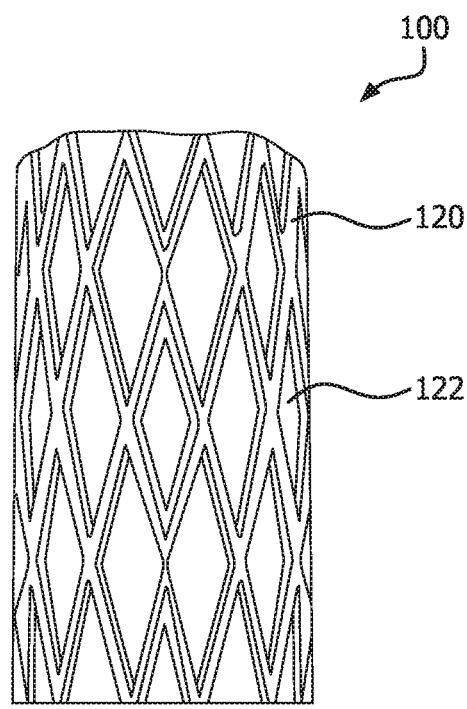
FIG. 1E is a representation of a valve in a compressed configuration.

In accordance with an embodiment of a transcatheter valve 100, with reference to FIGS. 1D-1E, the valve 100 may be compressed into a collapsed configuration having a smaller diameter and expanded into an expanded configuration so that the valve 100 can be endovascularly delivered in the collapsed configuration and expanded upon deployment within the tissue orifice 150 as shown in FIG. 4. The leaflet frame 130 and the outer frame 120 can be operable to recover circumferential uniformity when transitioning from the collapsed configuration to the expanded configuration.

The valve 100 may be mounted onto a delivery catheter, suitable for a particular purpose. The diameter of the valve 100 in the collapsed configuration is determined in part by the thickness of the leaflet frame 130 within the outer frame 120 and the leaflet thickness.

Other Considerations

Figure 10A:
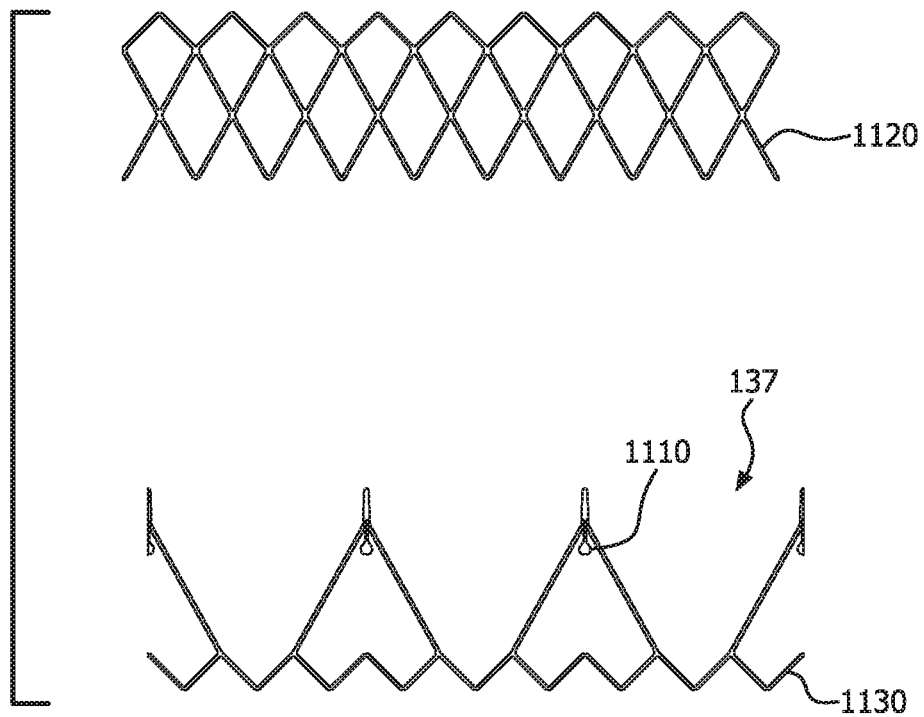
FIG. 10A is a side exploded view of a prosthetic valve comprising a leaflet frame having a generally tubular shape and an outer frame having a generally tubular shape that are coupled by a mechanic engagement member, in accordance with another embodiment.
Figure 10B:
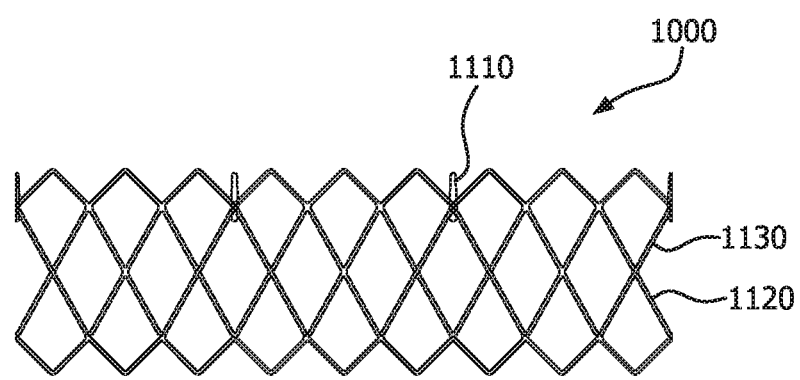
FIG. 10B is an assembled view of the embodiment of FIG. 10A.

FIGS. 10A and 10B are side exploded and assembled views, respectively, of a prosthetic valve 1000 comprising a leaflet frame 1130 having a generally tubular shape and an outer frame 1120 having a generally tubular shape that are coupled by a mechanic engagement member 1110, in accordance with another embodiment. The leaflet frame 1130 comprises an engagement member 1110 operable to engage the outer frame 1120 to affect coupling in which the leaflet frame 1130 is nested into the outer frame 1120 in a telescoping manner. The leaflet frame 1130 defines a plurality of leaflet windows 137, wherein film defines a leaflet extending from each of the leaflet windows 137.

In accordance with an embodiment, the valve 100 can be configured to prevent interference with a heart conduction system by not covering a bundle branch in the left ventricle when implanted, such as might be encountered with an aortic valve replacement procedure. For example, the valve 100 can comprise a length of less than about 25 mm or less than about 18 mm. The valve 100 can also comprise an aspect ratio of less than one, wherein the ratio describes the relationship between the length of the valve 100 to the expanded, functional diameter. However, the valve 100 can be constructed at any length and, more generally, any desirable dimension.

In a transcatheter embodiment, in a collapsed state, the valve 100 can have a collapsed profile that is less than about 35% of the expanded profile. For example, the valve 100 comprising a 26 mm expanded diameter can have a collapsed diameter of less than about 8 mm, or less than about 6 mm. The percent difference in diameter is dependent on dimensions and materials of the valve 100 and its various applications, and therefore, the actual percent difference is not limited by this disclosure.

The valve 100 can further comprise a bio-active agent. Bio-active agents can be coated onto a portion or the entirety of the film 160 for controlled release of the agents once the valve 100 is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Transcatheter Delivery System

In an embodiment, with reference to FIG. 4A, a valve delivery system 500 comprises a valve 100 having a collapsed configuration and an expanded configuration as previously described and an elongated flexible catheter 480, such as a balloon catheter, configured to deploy the valve 100 via endovascular access. The catheter 480 can comprise a balloon to expand the valve 100 and/or if required, to touch up the valve 100 to ensure proper seating. The valve 100 can be mounted to the distal section of the catheter 480 for delivery through the vasculature. In order to hold the valve in a collapsed configuration on the catheter 480, the valve delivery system may further comprise a removable sheath (not shown) to closely fit over the transcatheter valve 100.

A method of delivery can comprise the steps of radially compressing a valve into its collapsed configuration onto the distal end of an elongate flexible catheter having proximal and distal ends; delivering the valve to a tissue orifice, such as a native aortic valve orifice, via a transfemoral or transapical route, and expanding the valve into the tissue orifice. The valve can be expanded by inflating a balloon.

A method of delivery can comprise the steps of radially compressing a valve into its collapsed configuration, onto the distal section of an elongated flexible catheter having proximal and distal ends. A restraint, which can be connected to a tether that passes through the orifice of valve and the lumen of the catheter, is fitted around the posts of the valve. The valve is then delivered to a native valve orifice, such as a native aortic valve orifice, via a route of delivery and expanded into the native orifice. The route of delivery can comprise a transfemoral or transapical route. The valve can be expanded by inflating a balloon.

Surgical Embodiments

It is appreciated that the embodiments of the valve 100 may be surgically implanted rather than using transcatheter techniques. Embodiments of a surgically implanted valve 100 may be substantially the same as those described above, with the addition of a sewing cuff 171 adjacent to the outer frame outer surface 126a, shown in FIG. 4B, in accordance with an embodiment. The sewing cuff 171, which is well known in the art, is operable to provide structure that receives suture for coupling the valve 100 to an implant site, such as the tissue orifice. The sewing cuff 171 may comprise any suitable material, such as, but not limited to, double velour polyester. The sewing cuff 171 may be located circumferentially around the outer frame 120 or perivalvular depending from the outer frame 120.

Single Frame Valves

It is appreciated that embodiments of prosthetic valves are anticipated comprising the leaflet frame 130 and the film 160, without the outer frame 120. Referring to FIGS. 8D-8F, 11A-11B, embodiments of prosthetic valves comprising the leaflet frames 130f-130h are anticipated. The constructs of a single frame prosthetic valve in accordance with embodiments herein are provided suitable for a particular purpose. In accordance with embodiments of a surgically implanted valve having only the leaflet frame and film, may be substantially the same as those described above but without the outer frame, with the addition of a sewing cuff 171 shown in FIG. 4B, in accordance with an embodiment.

Method of Making

Figure 9A:
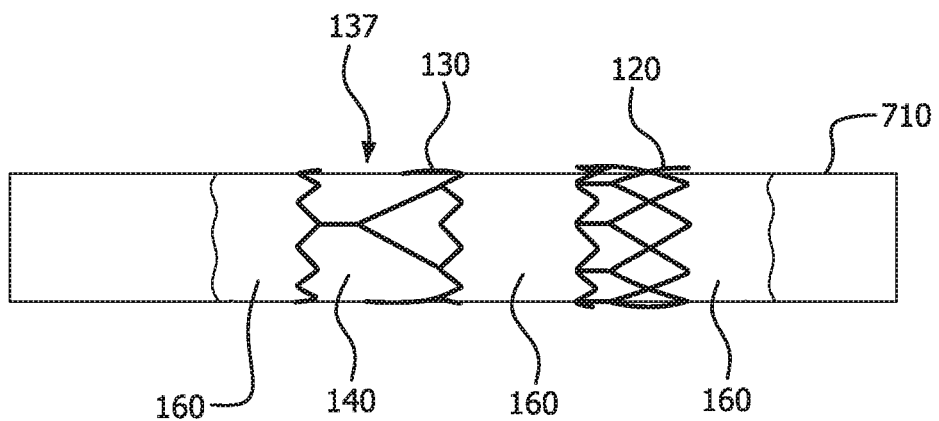
FIG. 9A is a side view of valve components on an assembly mandrel, in accordance with an embodiment.

Embodiments described herein also pertain to a method of making the valve 100 embodiments as described herein. In order to make the various embodiments, a cylindrical mandrel 710 can be used. With reference to FIG. 9A, the mandrel 710 comprises a structural form operable to receive the leaflet frame 130 and outer frame 120 thereon.

Figure 9B:
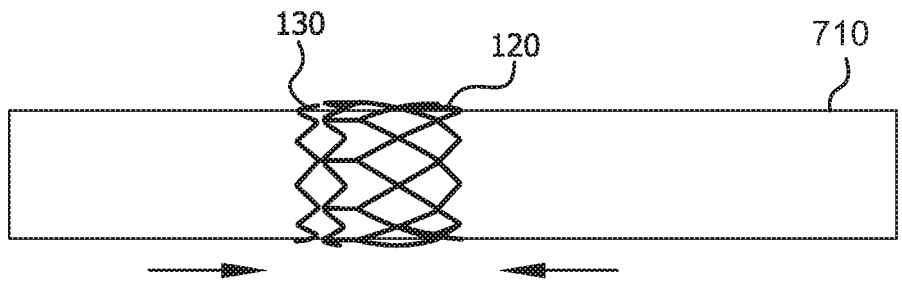
FIG. 9B is a side view of valve components on an assembly mandrel, in accordance with an embodiment.

With reference to FIGS. 9A-9B, an embodiment of a method of making a valve 100 comprises the steps of wrapping a first layer of film 160, e.g., a composite as described herein, into a tubular form about the mandrel 710; placing the leaflet frame 130 and outer frame 120 over the first layer of film 160, as shown in FIG. 9A; forming a second layer of film 160 over the leaflet frame 130 and the outer frame 120; thermally setting the assembly; cutting the film 160 across the leaflet window top within the leaflet window 137, masking with release material 170 a portion of the film 160 in the leaflet window that defines the leaflet 140 to prevent further bonding of leaflet 140 during subsequent processing steps; wrapping a second layer of film 160 into a tubular form over the leaflet frame 130, the outer frame 120, and over the first layer of film 160; thermal setting the assembly; remove the assembly from the mandrel, telescopically insert the leaflet frame into the outer frame; placing the assembly back on the mandrel; thermal setting the assembly to couple the leaflet frame 130 to the outer frame 120 in nesting engagement.

Figure 12:
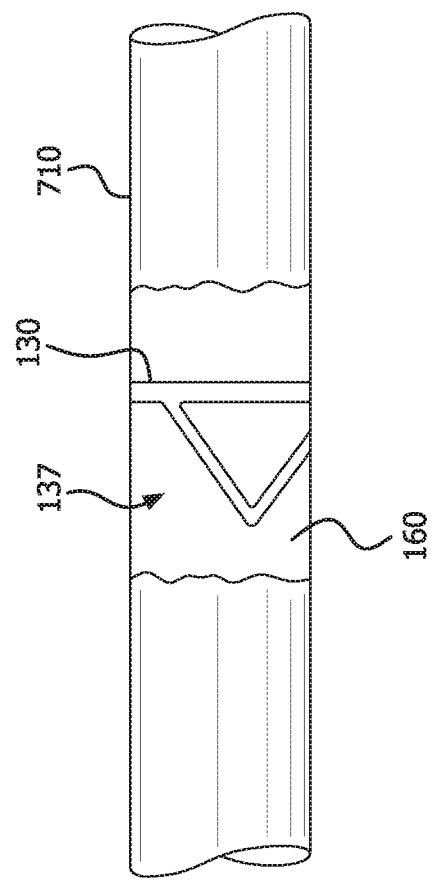
FIG. 12 is a side view of a leaflet frame on an assembly mandrel, in accordance with an embodiment.

Embodiments described herein also pertain to a method of making the valve 100 embodiments as described herein. In order to make the various embodiments, a cylindrical mandrel 710 can be used. With reference to FIG. 12, the mandrel 710 comprises a structural form operable to receive the leaflet frame 130 thereon. An embodiment of a method of making a valve 100 comprises the steps of wrapping a first layer of film 160, e.g., a composite as described herein, into a tubular form about the mandrel 710; placing the leaflet frame 130 over the first layer of film 160, as shown in FIG. 12; forming a second layer of film 160 over the leaflet frame 130; thermally setting the assembly; receiving the assembly over a cutting mandrel 712 as shown in FIGS. 13A and 13B; cutting the film 160 across the leaflet window top within the leaflet window 137, resulting in the valve 100 of FIG. 11B.

EXAMPLES

Example 1

A heart valve was produced having polymeric leaflets formed from a composite material having an expanded fluoropolymer membrane and an elastomeric material and joined between two collapsible metallic frames.

The leaflet frame and outer frame were laser machined from a length of SS316LVM tube hard tempered with an outside diameter of 23.0 mm and a wall thickness of 0.65 mm in the shape shown illustratively and generally indicated in FIG. 9A. The leaflet frame 130 and outer frame 120 were electro-polished resulting in 0.0127 mm material removal from each surface and leaving the edges rounded.

Fluorinated ethylene propylene (FEP) powder (Daikin America, Orangeburg N.Y.) was then applied to the leaflet frame 130 and outer frame 120. More specifically, the FEP powder was stirred to form an airborne "cloud" in an enclosed blending apparatus, such as a standard kitchen type blender, while the frames were suspended in the cloud. The frames were exposed to the FEP powder cloud until a uniform layer of powder was adhered to the entire surface of the frames. The frames were then subjected to a thermal treatment by placing it in a forced air oven set to 320° C. for approximately three minutes. This caused the powder to melt and adhere as a thin coating over the entire frame. The frames were removed from the oven and left to cool to room temperature.

Initial Assembly and Thermal Process Cycle

A 21 mm diameter vented metal cylindrical mandrel having a diameter corresponding to the inner diameter of the leaflet frame 130 and outer frame 120 was helically wrapped with sintered ePTFE fiber. A thin film of type 1 (ASTM D3368) FEP was constructed using melt extrusion and stretching. The type 1 (ASTM D3368) FEP film was about 40 μm thick and was about 7.7 cm wide. The mandrel was helically wrapped with one layer of this type 1 FEP film over the sintered ePTFE fiber only in the region of outer frame.

The mandrel was radially wrapped with five layers of an ePTFE membrane with an FEP coating towards the mandrel. The ePTFE membrane was manufactured according to the general teachings described in U.S. Pat. No. 7,306,729. The ePTFE membrane had a mass per area of 2.3 g/m², a bubble point of 101.5 MPa, a thickness of about 356 nm, a matrix tensile strength of 319 MPa in the longitudinal direction and 407 MPa in the transverse direction.

The mandrel was helically wrapped with one layer of type 1 FEP film.

The diameter of the leaflet frame and outer frame were expanded slightly and received on the wrapped mandrel with approximately a 10 mm space between them, rotational alignment was not necessary.

The leaflet frame, outer frame and the space therebetween were helically wrapped with 1 layer of type 1 FEP film.

The leaflet frame, outer frame and the space therebetween that will become the bridge portion 162, were circumferentially wrapped with 5 layers of the same ePTFE membrane with an FEP coating as described above with the coating toward the mandrel.

The wrapped leaflet frame, outer frame and the space therebetween were wrapped with several layers of an ePTFE membrane imbibed with a polyimide material referred to as a release liner.

A substantially nonporous ePTFE membrane was configured into a cylinder and placed over the assembly, referred to as sacrificial tube. Sintered ePTFE fiber was used to seal both ends of the sacrificial tube against the mandrel.

The assembly, including the mandrel, was heated in an oven capable of applying pneumatic pressure external to the sacrificial tube described above and while maintaining a vacuum internal to the mandrel for 40 min such that the mandrel temperature reached approximately 360° C. The assembly was removed from the oven and allowed to cool to room temperature while still pressurized and under vacuum.

The sacrificial tube and release liner was removed. The sintered ePTFE fiber was removed to release the frame assembly from the mandrel.

The polymeric material was trimmed and removed from the leaflet windows of the leaflet frame. The ends of each frame were circumferentially trimmed by a scalpel.

Intermediate Assembly and Thermal Process Cycle

An unsintered 15 mm diameter ePTFE tube was disposed on a 21.5 mm vented metal mandrel. Two layers of a substantially nonporous ePTFE membrane with a FEP coating was circumferentially wrapped on the mandrel with the coating side towards the mandrel. The wrapped mandrel was placed in a convection oven set to 320° C. and heated for 20 min. The ePTFE and substantially nonporous ePTFE membrane combined to serve as a release liner and was perforated to communicate pressure between the vent holes in the mandrel.

The leaflet frame was disposed onto the vented metal mandrel and vent holes were made in the apertures of the leaflet frame over the mandrel vent holes.

A leaflet material was then prepared. A membrane of ePTFE was manufactured according to the general teachings described in U.S. Pat. No. 7,306,729. The ePTFE membrane had a mass per area of 0.452 g/m², a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, MN) in a 2.5% concentration. The solution was coated using a Mayer bar onto the ePTFE membrane (while being supported by a polypropylene release film) and dried in a convection oven set to 145° C. for 30 seconds. After 2 coating steps, the final ePTFE/fluoroelastomer or composite had a mass per area of 1.75 g/m², 29.3% fluoropolymer by weight, a dome burst strength of about 8.6 KPa, and thickness of 0.81 μm.

The following test methods were used to characterize the ePTFE layers and the multi-layered composite. The thickness was measured with a Mutitoyo Snap Gage Absolute, 12.7 mm (0.50") diameter foot, Model ID-C112E, Serial #10299, made in Japan. The density was determined by a weight/volume calculation using an Analytical Balance Mettler PM400 New Jersey, USA. The force to break and tensile strengths were measured using an Instron Model #5500R Norwood, MA, load cell 50 kg, gage length=25.4 cm, crosshead speed=25 mm/minute (strain rate=100% per minute) with flat faced jaws. Unless otherwise noted, these test methods were used to generate the data in subsequent examples.

Ten layers of the composite leaflet material was wrapped around the leaflet frame with an elastomer rich side of the composite facing towards the mandrel. In exemplary embodiments, the composite material is oriented to have a predetermined matrix tensile strength along a direction generally perpendicular with the longitudinal axis of the combined tool assembly. More specifically, the predetermined matrix tensile strength is about 705 MPa.

The mandrel was radially wrapped with one layer of a substantially nonporous ePTFE membrane with an FEP coating towards the mandrel with a spacing 8 mm from the base of the leaflet frame. The ePTFE membrane was manufactured according to the general teachings described in U.S. Pat. No. 7,306,729. The ePTFE membrane had a mass per area of about 11 g/m$^2$, a thickness of about 5.5 µm, a matrix tensile strength of 310 MPa in the longitudinal direction and 103 MPa in the transverse direction.

A Kapton® (EI DuPont de Nemours, Inc., Wilmington, DE) polyimide film acting as a mask was wrapped over the substantially nonporous ePTFE membrane with an FEP coating layer.

The outer frame was placed on the mandrel with 10 mm spacing between the leaflet frame and the outer frame. The leaflet frame and the outer frame were aligned such that the longitudinal outer frame posts were collinear with the leaflet frame posts.

The leaflet frame and outer frame were wrapped with 24 layers of the composite leaflet material described earlier with an elastomer rich side of the composite facing towards the mandrel. In exemplary embodiments, the composite material is oriented to have a predetermined matrix tensile strength along a direction generally perpendicular with the longitudinal axis of the combined tool assembly. More specifically, the predetermined matrix tensile strength is about 705 MPa.

The final leaflet was comprised of 29.3% fluoropolymer by weight with a thickness of approximately 27 µm. Each leaflet had 34 layers of the composite and a ratio of thickness/number of layers of 0.8 µm.

The mandrel was again radially wrapped with one layer of a substantially nonporous ePTFE membrane with an FEP coating towards the mandrel with a spacing 8 mm from the base of the leaflet frame.

The assembly was wrapped with several layers of the sacrificial release liner. A sacrificial tube was placed over the assembly and sintered ePTFE fiber was used to seal both ends of the sacrificial tube against the mandrel.

The assembly was processed in an oven capable of applying pneumatic pressure external to the sacrificial material configured into a tube described above and while maintaining a vacuum internal to the tube for 25 min such that the mandrel temperature reached approximately 330° C. The assembly was removed from the oven and allowed to cool to room temperature while still pressurized and under vacuum.

The sacrificial tube and liner were removed from the frame assembly and the frame assembly was removed from the mandrel. The Kapton® mask was removed.

A scalpel was used to circumferentially trim the free edge of each leaflet and the distal end of leaflet frame.

Final Assembly and Thermal Process Cycle

The outer frame was radially expanded to a 24 mm diameter using a tapered mandrel.

A release liner as described above was placed on a 21.5 mm vented mandrel.

Three Kapton® masks were cut to the shape of leaflet window with a 30 mm tapered extension.

The frames with leaflet material were placed onto the mandrel and the tapered extensions of the Kapton® masks were inserted under the top ring of the leaflet frame from the trimmed end and were advanced axially until the masks aligned with the leaflet window.

The leaflet frame was wrapped with 2 layers of the type 1 FEP film.

A hot iron was used to remove the FEP film from the leaflet window region by melting it away from the perimeter and to tack the FEP film in all regions of leaflet frame outside the masks.

Vent holes were made within all the frame apertures and in the polymer tube region connecting the inner and outer frame.

While holding the leaflet frame in place, the outer frame was coaxially disposed over the leaflet frame by telescopically inverting the bridge portion of the contiguous tube.

The entire frame assembly was circumferentially wrapped with one substantially nonporous ePTFE membrane with an FEP coating towards the mandrel.

The assembly was wrapped with several layers of the sacrificial release liner. A sacrificial tube was placed over the assembly and sintered ePTFE fiber was used to seal both ends of the sacrificial tube against the mandrel.

The assembly was processed in an oven capable of applying pneumatic pressure external to the sacrificial material configured into a tube described above and while maintaining a vacuum internal to the tube for 25 min such that the mandrel temperature reached approximately 330° C. The assembly was removed from the oven and allowed to cool to room temperature while still pressurized and under vacuum.

The frame assembly was removed from the mandrel.

A scalpel was used to circumferentially trim each end of leaflet frame.

The Kapton was rotationally peeled away from inside the outer frame and away from leaflets.

Using scissors, both ends of the leaflet frame were trimmed to follow frame contour.

The resulting valve 100 includes leaflets 140 formed from a composite material with more than one fluoropolymer layer having a plurality of pores and an elastomer present in substantially all of the pores of the more than one fluoropolymer layer. Each leaflet 140 is movable between a closed position, shown in FIG. 3B, in which blood is substantially prevented from flowing through the valve assembly, and an open position, shown in FIG. 3A, in which blood is allowed to flow through the valve assembly. Thus, the leaflets 140 of the valve 100 cycle between the closed and open positions generally to regulate blood flow direction in a human patient.

The performance of the valve leaflets was characterized on a real-time pulse duplicator that measured typical anatomical pressures and flows across the valve. The flow performance was characterized by the following process:

The valve assembly was potted into a silicone annular ring (support structure) to allow the valve assembly to be subsequently evaluated in a real-time pulse duplicator. The potting process was performed according to the recommendations of the pulse duplicator manufacturer (ViVitro Laboratories Inc., Victoria BC, Canada)

The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 cm² cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, NC, USA.

In general, the flow pulse duplicator system uses a fixed displacement, piston pump to produce a desired fluid flow through the valve under test.

The heart flow pulse duplicator system was adjusted to produce the desired flow (5 L/min), mean pressure (15 mmHg), and simulated pulse rate (70 bpm). The valve under test was then cycled for about 5 to 20 minutes.

Pressure and flow data were measured and collected during the test period, including right ventricular pressures, pulmonary pressures, flow rates, and pump piston position. Shown illustratively in Figure XX is a graph of typical data outputs from the heart flow pulse duplicator system.

Parameters used to characterize the valve are effective orifice area and regurgitant fraction. The effective orifice area (EOA), which can be calculated as follows: $EOA(cm^2) = Q_{rms}/(51.6*(\Delta P)^{1/2})$ where $Q_{rms}$ is the root mean square systolic/diastolic flow rate (cm³/s) and $\Delta P$ is the mean systolic/diastolic pressure drop (mmHg).

Another measure of the hydrodynamic performance of a valve is the regurgitant fraction, which is the amount of fluid or blood regurgitated through the valve divided by the stroke volume.

The hydrodynamic performance measured values were; EOA=2.06 cm², and regurgitant fraction=8.2%.

Example 2

Another valve was made as described in Example 1 with the following exceptions.

Initial Assembly and Thermal Process Cycle

The diameter of the leaflet frame and outer frame were expanded slightly and received on the wrapped mandrel with 16 mm space between them, rotational alignment if the leaflet frame and outer frame was made.

Final Assembly and Thermal Process Cycle

A scalpel was used to cut above the mechanical linking tab. The tab was deformed to link inner and outer frames.

The resulting valve 100 includes leaflets 140 formed from a composite material with more than one fluoropolymer layer having a plurality of pores and an elastomer present in substantially all of the pores of the more than one fluoropolymer layer. Each leaflet 140 is movable between a closed position, shown in FIG. 3B, in which blood is substantially prevented from flowing through the valve assembly, and an open position, shown in FIG. 3A, in which blood is allowed to flow through the valve assembly. Thus, the leaflets 140 of the valve 100 cycle between the closed and open positions generally to regulate blood flow direction in a human patient.

The hydrodynamic performance was measured. The performance values were; EOA=2.3 cm² and regurgitant fraction=11.8%.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

Example 3 (Single Frame Valve)

In exemplary embodiments, a heart valve having polymeric leaflets formed from a composite material having an expanded fluoropolymer membrane and an elastomeric material and joined to a semi-rigid, non-collapsible metallic frame, and further a having strain relief was constructed according to the following process:

A leaflet frame was laser machined from a length of MP35N cobalt chromium tube hard tempered with an outside diameter of 26.0 mm and a wall thickness of 0.6 mm in the shape. The frame was electro-polished resulting in 0.0127 mm material removal from each surface and leaving the edges rounded. The frame was exposed to a surface roughening step to improve adherence of leaflets to the frame. The frame was cleaned by submersion in an ultrasonic bath of acetone for approximately five minutes. The entire metal frame surface was then subjected to a plasma treatment using equipment (e.g. PVA TePLa America, Inc Plasma Pen, Corona, CA) and methods commonly known to those having ordinary skill in the art. This treatment also served to improve the wetting of the fluorinated ethylene propylene (FEP) adhesive.

FEP powder (Daikin America, Orangeburg N.Y.) was then applied to the frame. More specifically, the FEP powder was stirred to form an airborne "cloud" in an enclosed blending apparatus, such as a standard kitchen type blender, while the frame is suspended in the cloud. The frame was exposed to the FEP powder cloud until a layer of powder was adhered to the entire surface of the frame. The frame was then subjected to a thermal treatment by placing it in a forced air oven set to 320° C. for approximately three minutes. This caused the powder to melt and adhere as a thin coating over the entire frame. The frame was removed from the oven and left to cool to approximately room temperature.

The strain relief was attached to the frame in the following manner. A thin (122 μm) walled sintered 15 mm diameter ePTFE tube was disposed on a 24.5 mm vented metal mandrel by stretching radially over a tapered mandrel. Two layers of a substantially nonporous ePTFE membrane with a continuous FEP coating was circumferentially wrapped on the mandrel with the FEP side towards the mandrel. The wrapped mandrel was placed in a convection oven set to 320° C. and heated for 20 min. The ePTFE and substantially nonporous ePTFE membrane combined to serve as an inner release liner and was perforated using a scalpel blade to communicate pressure between the vent holes in the mandrel. This entire release liner is removed in a later step.

A 5 cm length of the thick (990μ) walled partially sintered 22 mm inner diameter ePTFE tube (density=0.3 g/cm³) was disposed onto the 24.5 mm vented metal mandrel with release liner. The ePTFE tube inner diameter was enlarged by stretching it on a tapered mandrel to accommodate the larger mandrel diameter.

A thin (4 μm) film of type 1 FEP (ASTM D3368) was constructed using melt extrusion and stretching. One layer of the FEP was wrapped over the 5 cm length of the ePTFE tube.

The FEP powder coated frame was disposed onto the vented metal mandrel generally in the middle of the 5 cm span of ePTFE tube and FEP film.

One layer of the FEP was wrapped over the frame and 5 cm length of the ePTFE tube.

A second 5 cm length of the 990 μm thick/22 mm inner diameter ePTFE tube was disposed onto the assembly layered onto 24.5 mm vented metal mandrel by stretching its radius over a tapered mandrel to accommodate the larger construct diameter.

A substantially nonporous ePTFE membrane was configured into a cylinder at a diameter larger than the construct and placed over the assembly, referred to as sacrificial tube. Sintered ePTFE fiber (e.g. Gore Rastex® Sewing Thread, Part # S024T2, Newark Del.) was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 40 min such that the mandrel temperature reached approximately 360° C. (as measured by a thermocouple direct contact with the inner diameter of the mandrel). The assembly was removed from the oven and allowed to cool to approximately room temperature while still under 100 psi pressure and vacuum.

The sacrificial tube was then removed. Approximately 30 psi of pressure was applied to the internal diameter of the mandrel to assist in removal of the assembly. The inner release liner was peeled away from the internal diameter of the assembly by inverting the liner and axially pulling it apart.

The polymeric material was trimmed with a scalpel and removed from the leaflet windows and bottom of the frame leaving approximately 0.5 to 1.0 mm of material overhang.

A leaflet material was then prepared. A membrane of ePTFE was manufactured according to the general teachings described in U.S. Pat. No. 7,306,729. The ePTFE membrane had a mass per area of 0.452 g/m$^2$, a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, MN) in a 2.5% concentration. The solution was coated using a mayer bar onto the ePTFE membrane (while being supported by a polypropylene release film) and dried in a convection oven set to 145° C. for 30 seconds. After 2 coating steps, the final ePTFE/fluoroelastomer or composite had a mass per area of 1.75 g/m$^2$, 29.3% fluoropolymer by weight, a dome burst strength of about 8.6 KPa, and thickness of 0.81 μm.

The final leaflet was comprised of 28.22% fluoropolymer by weight with a thickness of 50.3 μm. Each leaflet had 26 layers of the composite and a ratio of thickness/number of layers of 1.93 μm.

The resulting valve assembly includes leaflets formed from a composite material with more than one fluoropolymer layer having a plurality of pores and an elastomer present in substantially all of the pores of the more than one fluoropolymer layer. Each leaflet is movable between a closed position, shown illustratively in FIG. 3B, in which blood is substantially prevented from flowing through the valve assembly, and an open position, shown illustratively in FIG. 3A, in which blood is allowed to flow through the valve assembly. Thus, the leaflets of the valve assembly cycle between the closed and open positions generally to regulate blood flow direction in a human patient.

The hydrodynamic performance was measured prior to accelerated wear testing. The performance values were; EOA=2.4 cm$^2$ and regurgitant fraction=11.94%.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed:

1. A prosthetic valve comprising:
a support structure having a longitudinal axis and defining a leaflet attachment zone between a pair of adjacent commissure posts, the pair of adjacent commissure posts defining a chord length; and
a leaflet coupled to and extending from the leaflet attachment zone, the leaflet having leaflet sides, a leaflet base, and a leaflet free edge opposite the leaflet base, the leaflet base and the leaflet sides being coupled to the support structure, the leaflet including a base segment defining a straight line that is shorter than the chord length and is adjacent to the leaflet base, the leaflet operable to bend about the base segment during opening-closing cycles associated with blood pressure differentials across the prosthetic valve, the prosthetic valve being operable to be reduced in diameter for transcatheter delivery and radially expanded for deployment.

2. The prosthetic valve of claim 1, wherein the leaflet is defined by a material coupled to an outer surface of the support structure.

3. The prosthetic valve of claim 1, wherein the leaflet is defined by a material coupled to an inner surface of the support structure.

4. The prosthetic valve of claim 1, wherein the leaflet is defined by a material coupled to an inner surface and an outer surface of the support structure.

5. The prosthetic valve of claim 1, wherein the leaflet includes a first film positioned inside the support structure and a second film positioned outside the support structure, the first film bonded to the second film.

6. The prosthetic valve of claim 1, wherein the leaflet is characterized by an absence of intersecting creases.

7. The prosthetic valve of claim 1, wherein the support structure comprises a plurality of frame elements spanning the leaflet attachment zone.

8. The prosthetic valve of claim 7, wherein the plurality of frame elements are associated with an outer frame positioned coaxially with the support structure.

9. The prosthetic valve of claim 1, wherein the leaflet is operable to bend along and about the base segment.

10. The prosthetic valve of claim 1, wherein the base segment is spaced from the leaflet attachment zone.

11. A prosthetic valve comprising:
a support structure having a longitudinal axis and defining a leaflet attachment zone between a pair of adjacent commissure posts; and a leaflet coupled to and extending from the leaflet attachment zone, the leaflet having leaflet sides, a leaflet base, and a leaflet free edge opposite the leaflet base, the leaflet base and the leaflet sides being coupled to the support structure, the leaflet including a straight base segment adjacent to the leaflet base, the leaflet including a planar zone having a planar zone base coincident with the straight base segment, the leaflet operable to bend about the straight base segment during opening-closing cycles associated with blood pressure differentials across the prosthetic valve, the prosthetic valve being operable to be reduced in diameter for transcatheter delivery and radially expanded for deployment.

12. The prosthetic valve of claim 11, wherein the pair of adjacent commissure posts defining a chord length, and wherein the straight base segment is shorter than the chord length.

13. The prosthetic valve of claim 11, wherein the straight base segment defines a virtual leaflet base about which a portion of the leaflet is operable to bend during opening and closing of the leaflet.

14. The prosthetic valve of claim 11, wherein the leaflet is defined by a material coupled to an inner surface and an outer surface of the support structure.

15. The prosthetic valve of claim 11, wherein the leaflet includes a first film positioned inside the support structure and a second film positioned outside the support structure, the first film bonded to the second film.

16. A prosthetic valve comprising:
a support structure having a longitudinal axis and defining a leaflet attachment zone between a pair of adjacent commissure posts; and
a leaflet coupled to and extending from the leaflet attachment zone, the leaflet having leaflet sides, a leaflet base, and a leaflet free edge opposite the leaflet base, the leaflet base and the leaflet sides being coupled to the support structure, the leaflet including a flat portion defining a shelf portion, the leaflet operable to bend from the flat portion along a straight base segment towards the free edge during opening-closing cycles associated with blood pressure differentials across the prosthetic valve, the prosthetic valve being operable to be reduced in diameter for transcatheter delivery and radially expanded for deployment.

17. The prosthetic valve of claim 16, wherein the leaflet is defined by a material coupled to an inner surface of the support structure.

18. The prosthetic valve of claim 16, wherein the support structure comprises a plurality of frame elements spanning the leaflet attachment zone.

19. The prosthetic valve of claim 18, wherein the plurality of frame elements are associated with an outer frame positioned coaxially with the support structure.

* * * * *